(12) United States Patent
Baile et al.

(10) Patent No.: US 8,101,213 B2
(45) Date of Patent: Jan. 24, 2012

(54) XANTHOHUMOL COMPOSITIONS AND METHODS OF USING SAME

(75) Inventors: Clifton A. Baile, Athens, GA (US); Mary Anne Della-Fera, La Veta, CO (US); Jeong-Yeh Yang, Athens, GA (US); Srujana Rayalam, Athens, GA (US); Hea Jin Park, Tolland, CT (US)

(73) Assignee: The University of Georgia Research Foundation, Inc, Athens, GA (US)

( * ) Notice: Subject to any disclaimer, the term of this patent is extended or adjusted under 35 U.S.C. 154(b) by 607 days.

(21) Appl. No.: 12/209,681

(22) Filed: Sep. 12, 2008

(65) Prior Publication Data
US 2009/0075957 A1    Mar. 19, 2009

Related U.S. Application Data

(60) Provisional application No. 60/993,568, filed on Sep. 13, 2007.

(51) Int. Cl.
*A61K 36/00* (2006.01)
*A61K 31/56* (2006.01)
*A61K 31/35* (2006.01)
*A61K 31/045* (2006.01)

(52) U.S. Cl. ........ 424/725; 514/177; 514/456; 514/728; 514/909

(58) Field of Classification Search .................. 424/725; 514/177, 456, 728, 909
See application file for complete search history.

(56) References Cited

FOREIGN PATENT DOCUMENTS
JP    2006306800 A  * 11/2006

OTHER PUBLICATIONS

Enclosed English-translated Abstract of JP 2006306800A (2006).*
Kim et al., "Genistein Decreases Food Intake, Body Weight, and Fat Pad Weight and Causes Adipose Tissue Apoptosis in Ovariectomized Female Mice", The Journal of Nutrition, vol. 136, No. 2, pp. 409-414 (2006).*

* cited by examiner

*Primary Examiner* — Kevin E Weddington
(74) *Attorney, Agent, or Firm* — Henry D. Coleman; R. Neil Sudol; William J. Sapone

(57) ABSTRACT

The present invention provides compositions comprising an effective amount of xanthohumol and honokiol. The present invention comprises compositions comprising an effective amount of xanthohumol and genistein. The present invention comprises compositions comprising an effective amount of xanthohumol and guggulsterone. The compositions of the present invention may be effective to decrease mature adipocytes viability, induce apoptosis of mature adipocytes, increase lipolysis in mature adipocytes, and/or reduce adipogenesis during the maturation of pre-adipocytes. The present invention further provides methods of treating obesity, diabetes, osteoporosis or bone disorders in a subject, which comprise administering to the subject compositions comprising an effective amount of xanthohumol and honokiol, guggulsterone, or genistein.

5 Claims, 15 Drawing Sheets

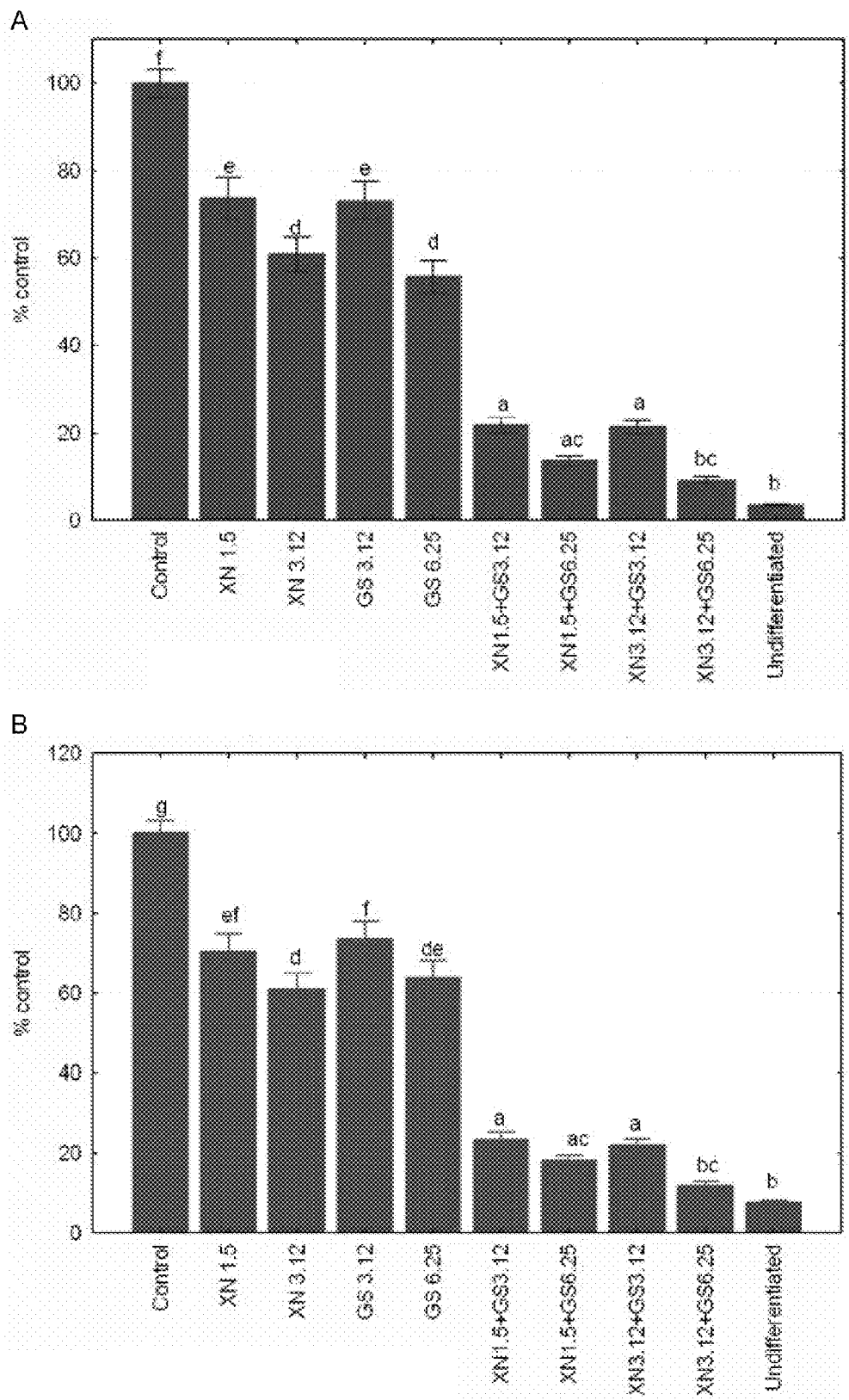
FIGURE 15A-B

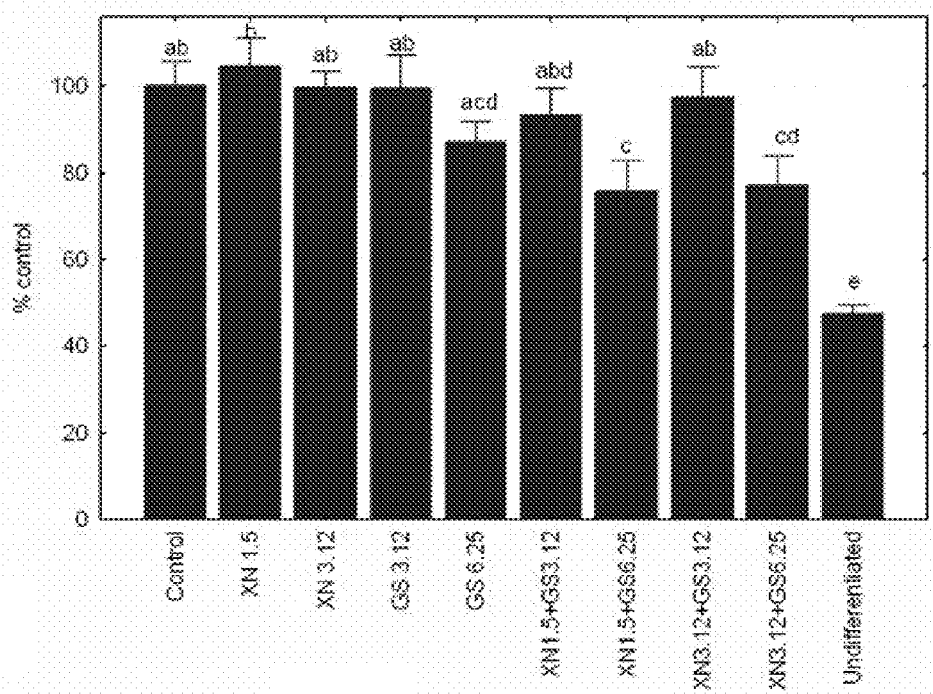
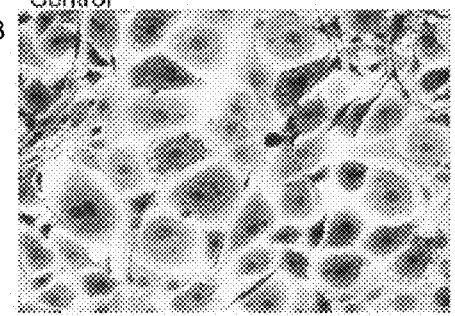
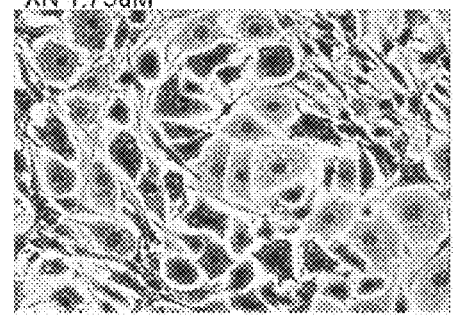
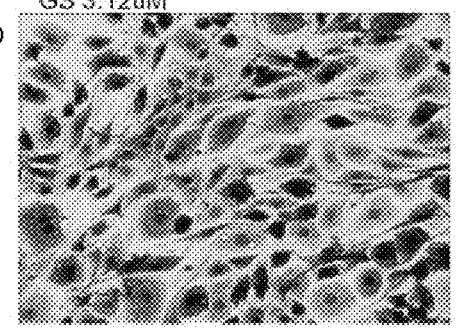
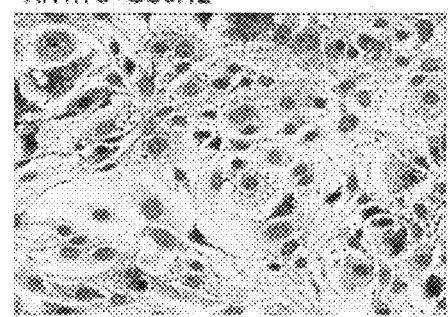
FIGURE 16A-E

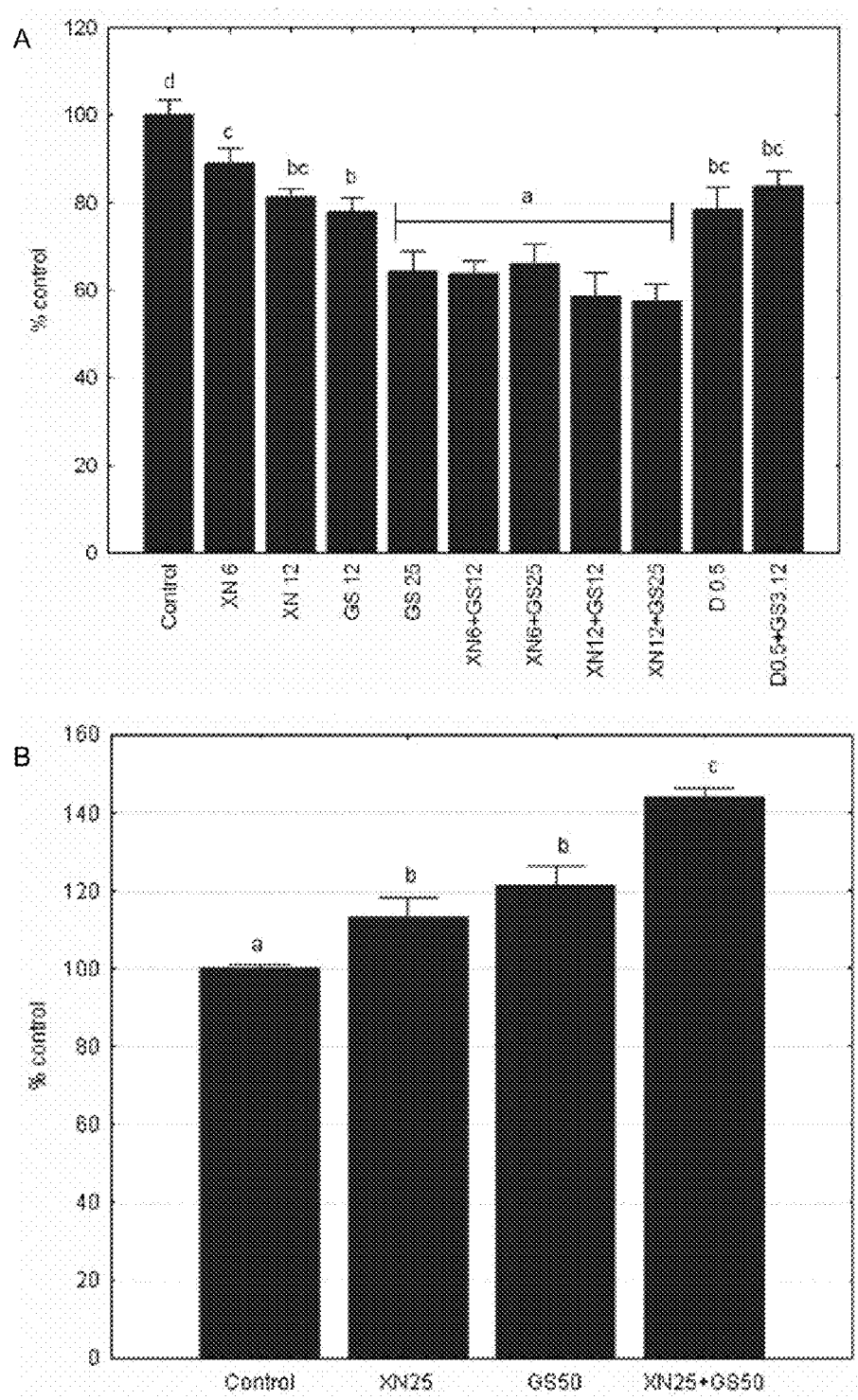
FIGURE 17A-B

XANTHOHUMOL COMPOSITIONS AND METHODS OF USING SAME

CROSS REFERENCE TO RELATED PATENT APPLICATIONS

The present invention claims the priority of U.S. Provisional Patent Application Ser. No. 60/993,568, filed Sep. 13, 2007, which is herein incorporated in its entirety.

TECHNICAL FIELD

The present invention relates to pharmaceutical compositions comprising an effective amount of xanthohumol and honokiol, guggulsterone, or genistein, and methods of using the same, particularly methods of treating and/or preventing conditions, including, without limitation, obesity, diabetes, osteoporosis, and other bone disorders, as well as methods of inducing apoptosis of cells in adipose tissue and bone marrow.

BACKGROUND OF THE INVENTION

Obesity is a complex condition that is increasingly affecting the population worldwide. According to the World Health Organization (WHO), there were an estimated 1.6 billion adults who were classified as overweight in 2005, and at least 400 million adults of these adults were considered obese. In addition, 20 million children under the age of five were classified as overweight in 2005. The WHO further projects that by 2015, approximately 2.3 billion adults will be overweight and more than 700 million will be obese.

Both congenital and environmental factors, such as exercise and eating habits, contribute to this disease. In addition to affecting the lifestyle of an individual, obesity can lead to a number of complications and diseases, including hypertension, stroke, type II diabetes, gallbladder disease, cardiovascular disease, hyperlipidemia, sleep apnea, coronary artery disease, joint osteoarthritis, gout, infertility, and cancer. Its health consequences range from increased risk of premature death to serious chronic conditions that reduce the overall quality of life.

Diabetes mellitus is a heterogeneous group of disorders characterized by high blood glucose levels. Type 1 or insulin-independent diabetes results from a deficiency of insulin due to destruction of the insulin-producing pancreatic $\beta$-cell islets. People who suffer from type 1 diabetes have to take exogenous insulin to prevent the development of ketoacidosis. In type 2 or non-insulin-dependent diabetes mellitus, muscle, fat, and liver cells become resistant to the actions of insulin. In addition, the mechanisms that are activated in $\beta$-cells to secrete insulin to maintain blood glucose levels within a normal physiological range fail to function properly. Type 2 diabetes accounts for about 90% of all diabetes cases.

Diabetes is a potentially dangerous disease because it is associated with marked increases in the incidence of coronary, cerebral, and peripheral artery disease. As a result, patients with diabetes have a much higher risk of developing other disorders such as myocardial infarction, stroke, limb amputation, renal failure, or blindness. Atherosclerotic cardiovascular disease is responsible for 80% of diabetic mortality and more than 75% of all hospitalizations for diabetic complications.

Obesity and type 2 diabetes are highly correlated conditions. For example, an obese animal, such as a human, is at a high risk of developing type 2 diabetes. What is needed are compositions and methods for treatment of obesity and or diabetes.

Approximately 10 million people in the U.S. are estimated to have osteoporosis, a disease that results in over 1.5 million bone fractures a year. The direct expenditures for osteoporosis in 2001 totaled $17 billion, which equals a cost of $47 million per day. Osteoporosis is therefore a significant health problem. The accumulation of adipocytes in bone marrow is believed to be a major factor contributing to age-related bone loss. For example, women with osteoporosis have higher numbers of marrow adipocytes than women with healthy bone, and bone formation rate is inversely correlated with adipocyte number in bone tissue biopsies from both men and women. Thus, what is needed are compositions and methods for treatment of osteoporosis and other bone disorders.

SUMMARY

The present invention generally comprises compositions comprising an effective amount of xanthohumol and honokiol, guggulsterone or genistein, and methods for making and using the same.

An aspect of the present invention comprises a composition comprising xanthohumol and at least one of honokiol, genistein, or guggulsterone. In an embodiment of the present invention, a composition may further comprise a pharmaceutically-acceptable carrier. In an embodiment of the present invention, xanthohumol and at least one of honokiol, genistein, or guggulsterone can comprise an effective amount of xanthohumol and at least one of honokiol, genistein, or guggulsterone to affect at least one biological process, wherein at least one of the at least one biological process is adipocyte viability, adipocyte apoptosis, lipolysis in adipocytes, or adipogenesis.

In one aspect, the present invention provides a composition comprising an effective amount of xanthohumol and honokiol. In one embodiment, the composition of the present invention may comprise xanthohumol and honokiol in an effective amount to decrease mature adipocytes viability and/or induce apoptosis of mature adipocytes. In another embodiment, the composition of the present invention may comprise xanthohumol and honokiol in an effective amount to increase lipolysis in mature adipocytes. In yet another embodiment, the composition of the present may comprise xanthohumol and honokiol in an effective amount to reduce adipogenesis during the maturation of lipid cells.

In another aspect, the present invention provides a composition comprising an effective amount of xanthohumol and genistein. In one embodiment, the composition of the present invention may comprise xanthohumol and genistein in an effective amount to decrease mature adipocyte viability and/or induce apoptosis of mature adipocytes.

In another aspect, the present invention provides a composition comprising an effective amount of xanthohumol and guggulsterone. In one embodiment, the composition of the present invention may comprise xanthohumol and guggulsterone in an effective amount to induce apoptosis and inhibit adipogenesis, such as that shown in 3T3-L1 adipocytes.

An aspect of the present invention comprises a method of treating obesity in a subject, the method comprising administering to a subject a composition comprising an effective amount of xanthohumol and at least one of honokiol, guggulsterone or genistein. In an embodiment of the present invention, the method may further comprise decreasing the viability of adipocytes in the subject. In an embodiment of the present invention, the method may further comprise increasing adipocyte apoptosis in the subject. In an embodiment of the present invention, the method may further comprise increasing lipolysis in adipocytes of the subject. In an embodiment of the present invention, the method can further comprise decreasing adipogenesis in pre-adipocytes of the subject.

An aspect of the present invention comprises a method of treating diabetes in a subject by affecting the weight of the subject, the method comprising administering to a subject a composition comprising an effective amount of xanthohumol and at least one of honokiol, guggulsterone or genistein. In an embodiment of the present invention, the method may further comprise decreasing the viability of adipocytes in the subject. In an embodiment of the present invention, the method may further comprise increasing adipocyte apoptosis in the subject. In an embodiment of the present invention, the method may further comprise increasing lipolysis in adipocytes of the subject. In an embodiment of the present invention, the method may further comprise decreasing adipogenesis in pre-adipocytes of the subject.

An aspect of the present invention comprises a method of treating bone disorders in a subject, the method comprising administering to a subject a composition comprising an effective amount of xanthohumol and at least one of honokiol, guggulsterone or genistein. In an embodiment of the present invention, the method may further comprise decreasing the viability of adipocytes in the subject. In an embodiment of the present invention, the method may further comprise increasing adipocyte apoptosis in the subject. In an embodiment of the present invention, the method may further comprise increasing lipolysis in adipocytes of the subject. In an embodiment of the present invention, the method may further comprise decreasing adipogenesis in pre-adipocytes of the subject.

An aspect of the present invention comprises a method of treating fat deposits in a subject, the method comprising administering to a subject a composition comprising an effective amount of xanthohumol and at least one of honokiol, guggulsterone or genistein. In an embodiment of the present invention, the method may further comprise decreasing the viability of adipocytes in the subject. In an embodiment of the present invention, the method may further comprise increasing adipocyte apoptosis in the subject. In an embodiment of the present invention, the method may further comprise increasing lipolysis in adipocytes of the subject. In an embodiment of the present invention, the method may further comprise decreasing adipogenesis in pre-adipocytes of the subject.

Other features and advantages of the present invention will become apparent from the following detailed description. It should be understood, however, that the detailed description and the specific examples, while indicating the preferred embodiments of the present invention, are given by way of illustration only, since various changes and modifications within the spirit and scope of the present invention will become apparent to those skilled in the art from this detailed description.

DESCRIPTION OF FIGURES

FIG. 15A and B are graphs that shows the effect of xanthohumol and guggulsterone on adipogenesis in inhibiting lipid accumulation in maturing 3T3-L1 adipocytes.

FIG. 16A is a graph that shows the effect of xanthohumol and guggulsterone on viability in maturing pre-adipocytes cell viability. The means denoted by common letters are significantly different ($P<0.05$).

FIG. 16B-E are micrographs of maturing pre-adipocytes treated with test compounds and stained with Oil Red O to visualize triglyceride accumulation.

FIG. 17A-B is a graph that shows the effect of xanthohumol and guggulsterone on lipolysis.

DETAILED DESCRIPTION

Figure 1:
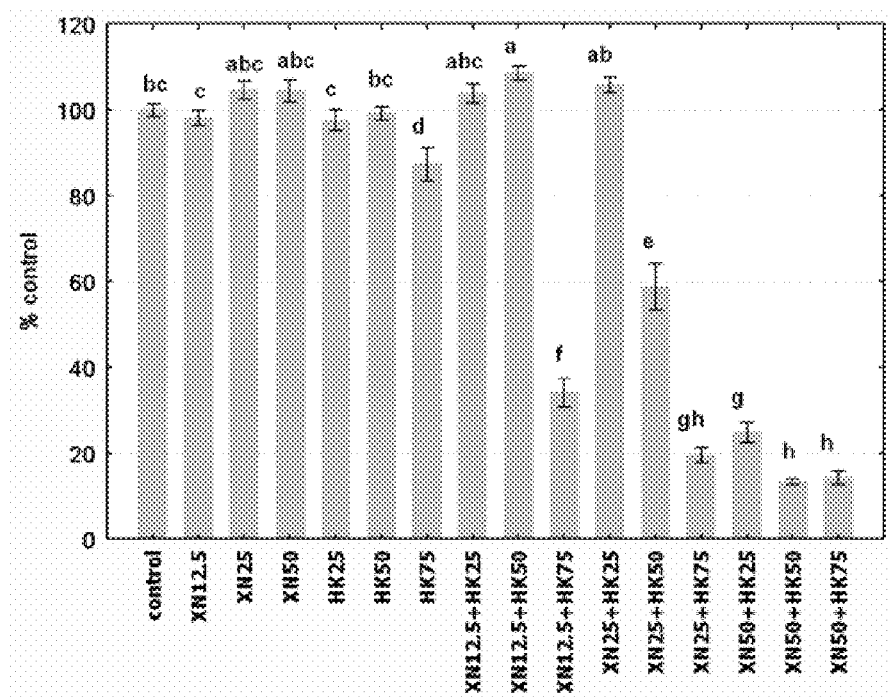
FIG. 1 is a graph that shows the effects of xanthohumol and honokiol on the viability of mature adipocytes.

The present invention comprises effective compositions and methods for the treatment and prevention of various pathological conditions, such as, obesity, diabetes, osteoporosis, and other bone disorders. The compositions of the present invention comprise a combination of xanthohumol and honokiol, or xanthohumol and guggulsterone, or xanthohumol and genistein in an effective amount to decrease mature adipocytes viability, induce apoptosis of mature adipocytes. Though not wishing to be bound by any particular theory, it is theorized that the compositions of the present invention act by activation of caspase 3 and/or 7, increase the release of cytochrome c from mitochondria, increase the level of DNA breakage, enhance PARP cleavage in mature adipocytes, increase lipolysis in mature adipocytes, reduce adipogenesis during the maturation of pre-adipocytes, or combinations thereof.

Xanthohumol (which may be hereinafter referred to as "XN") is a prenylated chalcone compound that occurs in the hop plant, *Humulus lupulus* L. (Cannabaceae), where it is the principal prenylflavonoid of the female inflorescences. Honokiol (which may be hereinafter referred to as "HK") is a small molecular weight lignan originally isolated from the Chinese medicinal herb, *Magnolia officinalis*, which has been used as muscle relaxant for almost three decades. Genistein (4,5,7-trihydroxyisoflavone) (which may be hereinafter referred to as "G") is the most abundant isoflavone found in soybeans. It is also classified as a phytoestrogen, which are plant-derived nonsteroidal compounds that possess estrogen-like biological activity. Guggulsterone (which may be hereinafter referred to as "GS") is the active substance in guggulipid, an extract of the guggul tree, *Commiphora mukul*. The stereoisomers E- and Z-guggulsterone have been identified as the active agents in this resin.

In one aspect, the present invention provides a composition, which contains an effective amount of xanthohumol and honokiol. Both xanthohumol and honokiol are commercially available. In one embodiment, xanthohumol/honokiol may be isolated or may comprise substantially pure xanthohumol/honokiol. Xanthohumol/honokiol, suitable for the purposes of the present invention, may be of natural, synthetic, or semi-synthetic origin. The compositions of the present invention may further comprise a pharmaceutically acceptable carrier. In one embodiment, the composition of the present invention may be a pharmaceutical composition.

Xanthohumol, a diacylglycerol acyltransferase inhibitor, has been shown to inhibit the synthesis of triglycerides and the generation of lipid droplets in cytoplasm. In addition, xanthohumol may inhibit microsomal triglyceride transfer protein (MTP) related to the lowering effects of triglyceride and apolipoprotein B. Xanthohumol has also been shown to have anti-cancer properties. It is reported that xanthohumol induced apoptosis in cancer cells.

Honokiol has been demonstrated to induce anti-angiogenic activities in human endothelial cells in vitro and was highly effective against angiosarcoma in nude mice. Honokiol has also been shown to inhibit tumor invasiveness in vitro, possibly by inhibiting matrix metalloproteinase-9 (MMP-9) activity. In addition, honokiol was found to exhibit anti-proliferative and apoptotic activities against a variety of tumor cells, including leukemia, multiple myeloma, and squamous lung cancer.

In one embodiment, the composition of the present invention may comprise xanthohumol and honokiol in an effective amount to decrease mature adipocyte viability. The composition of the present invention may reduce viability of mature adipocytes by inducing apoptosis of mature adipocytes. For example, a combination of xanthohumol and honokiol may modulate the function, subcellular localization, and/or level of various key apoptosis-related effectors, such as, without limitation, caspases 3 and 7, and cytochrome c. The xanthohumol and honokiol-containing composition of the present invention may enhance the cleavage of PARP in mature adipocytes.

In another embodiment, the composition of the present invention may comprise xanthohumol and honokiol in an effective amount to increase lipolysis in mature adipocytes.

In yet another embodiment, the composition of the present invention may comprise xanthohumol and honokiol in an effective amount to reduce adipogenesis during the maturation of pre-adipocytes.

A composition of the present invention may comprise an effective amount of xanthohumol, which may result in a dose of xanthohumol of about 0.001 µg/kg to about 1,000 mg/kg, and an effective amount of honokiol, which may result in a dose of honokiol of about 0.001 µg/kg to about 1,000 mg/kg when administered to an in vivo or in vitro system, for example, a system of cultured cells, a human, or an animal. In an embodiment of the present invention, the concentration of xanthohumol can comprise about 3 µM to about 50 µM. In an embodiment of the present invention, an effective amount of xanthohumol may comprise about 0.01 µg/kg to about 100 mg/kg, or about 1 µg/kg to about 10 mg/kg. In an embodiment of the present invention, the concentration of honokiol can comprise about 6 µM to about 75 µM. In an embodiment of the present invention, an effective amount of honokiol may comprise about 0.01 µg/kg to about 100 mg/kg, or about 1 µg/kg to about 10 mg/kg.

In another aspect, the present invention provides a composition comprising an effective amount of xanthohumol and genistein. Genistein, suitable for the purposes of the present invention, may be of natural, synthetic, or semi-synthetic origin, and may be in an isolated or substantially pure form. In one embodiment, the composition of the present invention may comprise xanthohumol and genistein in an effective amount to decrease mature adipocyte viability and/or induce apoptosis of mature adipocytes. Not wishing to be bound by any particular theory, it is theorized that the composition may act by an increase in the level of DNA breakage in mature adipocytes. The composition of the present invention may further comprise a pharmaceutically acceptable carrier. In one embodiment, the composition of the present invention may be a pharmaceutical composition.

Genistein has a heterocyclic diphenolic structure similar to estrogen and has demonstrated anti-tumor and anti-angiogenic activities. Genistein has been shown to inhibit cell growth of tumor cell lines from various malignancies, including breast, lung, melanoma, prostate, head and neck squamous cell carcinoma, leukemia, and lymphoma. Radiation-induced activation of NF-κB activity was strongly inhibited by genistein pre-treatment. Pre-treatment of PC-3 cells with genistein for 24 hr followed by radiation showed that NF-κB DNA binding activity was significantly inhibited. A significant and striking increase in cleaved PARP protein was also detected following combined genistein and radiation treatment, indicating increased apoptosis.

In one embodiment, the composition of the present invention may comprise an effective amount of xanthohumol and genistein, which may yield a dose of xanthohumol of about 0.001 µg/kg to about 1,000 mg/kg of xanthohumol and an effective amount of genistein, which may yield a dose of genistein of about 0.001 µg/kg to about 1,000 mg/kg when administered to an in vivo or in vitro system, for example, a system of cultured cells, a human, or an animal. In an embodiment of the present invention, the concentration of xanthohumol can comprise about 25 µM to about 50 µM. In an embodiment of the present invention, an effective amount of xanthohumol may comprise about 0.01 µg/kg to about 100 mg/kg, or about 1 µg/kg to about 10 mg/kg. In an embodiment of the present invention, the concentration of genistein can comprise about 50 µM to about 100 µM. In an embodiment of the present invention, an effective amount of genistein may comprise about 0.01 µg/kg to about 100 mg/kg, or about 1 µg/kg to about 10 mg/kg.

In another aspect, the present invention provides a composition comprising an effective amount of xanthohumol and guggulsterone. Recent studies have shown that both the isomers of guggulsterone are antagonist ligands for the bile acid receptor farnesoid X receptor (FXR). Guggulsterone was also shown to exhibit anti-inflammatory activities by suppressing NF-κB and NF-κB-regulated gene products.

Guggulsterone, suitable for the compositions and methods of the present invention, may be of natural, synthetic, or semi-synthetic origin, may be in an isolated or substantially pure form, and may include mixtures of stereoisomers or purified stereoisomers of guggulsterone. In one embodiment, the composition of the present invention may comprise xanthohumol and guggulsterone in an effective amount to increase apoptosis and inhibit adipogeneis in adipocytes, inhibit lipid accumulation in maturing adipocytes, and effect LDH release, increase caspase activation, decrease Bcl2, and induce lipolysis. The composition of the present invention may further comprise a pharmaceutically acceptable carrier. In one embodiment, the composition of the present invention may be a pharmaceutical composition.

In one embodiment, the composition of the present invention may comprise an effective amount of xanthohumol, which may yield a dose of xanthohumol of about 0.001 µg/kg to about 1,000 mg/kg and an effective amount of guggulsterone, which may yield a dose of guggulsterone of about 0.001 µg/kg to about 1,000 mg/kg when administered to an in vivo or in vitro system, for example a system of cultured cells, a human, or an animal. In an embodiment of the present invention, the concentration of xanthohumol can comprise about 25 µM to about 100 µM. In an embodiment of the present invention, an effective amount of xanthohumol may comprise about 0.01 µg/kg to about 100 mg/kg, or about 1 µg/kg to about 10 mg/kg. In an embodiment of the present invention, the concentration of guggulsterone can comprise about 25 µM to about 100 µM. In an embodiment of the present invention, an effective amount of guggulsterone may comprise about 0.01 µg/kg to about 100 mg/kg, or about 1 µg/kg to about 10 mg/kg.

In one embodiment, a composition of the present invention comprises xanthohumol and at least one of honokiol, genistein, or guggulsterone. In another embodiment, a composition of the present invention comprises xanthohumol and at least two of honokiol, genistein, or guggulsterone. In yet another embodiment of the present invention, a composition of the present invention comprises xanthohumol, honokiol, genistein, and guggulsterone.

The present invention further comprises methods of treating or preventing obesity and/or diabetes in a subject, which comprise administering to the subject a composition comprising a pharmaceutically acceptable carrier and an effective amount of xanthohumol and honokiol, xanthohumol and guggulsterone, or xanthohumol and genistein.

An aspect of the present invention comprises a method of treating obesity in a subject, the method comprising administering to a subject a composition comprising an effective amount of xanthohumol and at least one of honokiol, guggulsterone or genistein. The method may further comprise decreasing the viability of adipocytes in the subject. In an embodiment of the present invention, the method may comprise increasing adipocyte apoptosis in the subject. The method may also comprise increasing lipolysis in adipocytes of the subject. In an embodiment of the present invention, the method can further comprise decreasing adipogenesis in pre-adipocytes of the subject.

An aspect of the present invention comprises a method of treating diabetes in a subject by affecting the weight of the subject, the method comprising administering to a subject a composition comprising an effective amount of xanthohumol and at least one of honokiol, guggulsterone or genistein. In an embodiment of the present invention, the method may further comprise decreasing the viability of adipocytes in the subject. In an embodiment of the present invention, the method may further comprise increasing adipocyte apoptosis in the subject. In an embodiment of the present invention, the method may further comprise increasing lipolysis in adipocytes of the subject. In an embodiment of the present invention, the method may further comprise decreasing adipogenesis in pre-adipocytes of the subject.

The accumulation of adipocytes in bone marrow is believed to be a major factor contributing to age-related bone loss. For example, women with osteoporosis have higher numbers of marrow adipocytes than women with healthy bone, and bone formation rate is inversely correlated with adipocyte number in bone tissue biopsies from both men and women. Recent in vivo and in vitro studies provide insights into why marrow adipogenesis is associated with bone loss. For example, mesenchymal stem cells within bone marrow can differentiate to form adipocytes or osteoblasts. Conditions favoring adipocyte differentiation will therefore have adverse effects on bone formation because precursor cells are directed towards the adipocyte lineage rather than the osteoblast lineage. In addition, adipocytes secrete osteoclastogenic cytokines, such as IL-6, and adipocytes can inhibit osteoblast activity in culture. Fat cell development and hypertrophy can also compress intraosseous capillaries, which decreases blood supply within bone. Thus, removal of adipocytes from bone marrow through induction of apoptosis may prevent or reverse bone loss associated with osteoporosis.

An aspect of the present invention comprises a method of treating bone disorders in a subject, the method comprising administering to a subject a composition comprising an effective amount of xanthohumol and at least one of honokiol, guggulsterone or genistein. In an embodiment of the present invention, the method may further comprise decreasing the viability of adipocytes in the subject. In an embodiment of the present invention, the method may further comprise increasing adipocyte apoptosis in the subject. In an embodiment of the present invention, the method may further comprise increasing lipolysis in adipocytes of the subject. In an embodiment of the present invention, the method may further comprise decreasing adipogenesis in pre-adipocytes of the subject.

Liposuction and surgical excision of subcutaneous fat deposits are increasingly popular procedures for treatment of excessive localized fat tissue. However, these procedures are costly and carry increased risk of side effects ranging from localized infection and inflammation to death resulting from fat embolism to the lung.

An aspect of the present invention comprises a method of treating fat deposits in a subject, the method comprising administering to a subject a composition comprising an effective amount of xanthohumol and at least one of honokiol, guggulsterone or genistein. In an embodiment of the present invention, the method may further comprise decreasing the viability of adipocytes in the subject. In an embodiment of the present invention, the method may further comprise increasing adipocyte apoptosis in the subject. In an embodiment of the present invention, the method may further comprise increasing lipolysis in adipocytes of the subject. In an embodiment of the present invention, the method may further comprise decreasing adipogenesis in pre-adipocytes of the subject. The method may comprise injection of the compounds of the present invention in the fat deposit of interest.

As used herein, the term "treat" includes, without limitation, ameliorating, reducing, minimizing, controlling, or changing a physiological or pathological condition associated with, or a clinical impairment or symptom resulting from or related to, diabetes and/or obesity. For example, the clinical impairment or symptom of diabetes may be ameliorated or minimized by diminishing any pain or discomfort suffered by the subject; by extending the survival of the subject beyond that which would otherwise be expected in the absence of such treatment; by inhibiting or preventing the development of diabetic symptoms in the subject; or by limiting, suspending, terminating, or otherwise controlling the growth of adipose tissue in the subject. As used herein, the term "subject" includes, without limitation, a mammal (such as, a cow, dog, cat, human, monkey, mouse, pig, or rat), a bird, and an amphibian. In one embodiment, the subject may be a human.

The pharmaceutically-acceptable carrier may be "acceptable" in the sense of being compatible with the other ingredients of the composition, and not deleterious to the recipient thereof The pharmaceutically-acceptable carrier employed herein may be selected from various organic or inorganic materials that are used in pharmaceutical formulations, and which may be incorporated as analgesic agents, buffers, binders, disintegrants, diluents, emulsifiers, excipients, extenders, glidants, solubilizers, stabilizers, suspending agents, tonicity agents, vehicles, and/or viscosity-increasing agents. If necessary, pharmaceutical additives, such as antioxidants, aromatics, colorants, flavor-improving agents, preservatives, and sweeteners, may also be added. Examples of acceptable pharmaceutical carriers include carboxymethyl cellulose, crystalline cellulose, glycerin, gum arabic, lactose, magnesium stearate, methyl cellulose, powders, saline, sodium alginate, sucrose, starch, talc, and water, among others.

The pharmaceutical composition of the present invention may be prepared by methods well-known in the pharmaceutical arts. For example, the composition may be brought into association with a carrier or diluent, as a suspension or solution. Optionally, one or more accessory ingredients (e.g., buffers, flavoring agents, surface active agents, and the like) also may be added. The choice of carrier will depend upon the route of administration of the composition. Formulations of the composition may be conveniently presented in unit dosage, or in such dosage forms as aerosols, capsules, elixirs, emulsions, eye drops, injections, liquid drugs, pills, powders, granules, suppositories, suspensions, syrup, tablets, or troches, which can be administered orally, topically, or by injection, including, without limitation, intravenous, intraperitoneal, subcutaneous, intramuscular, and intratumoral (i.e., direct injection into the tumor) injection.

The pharmaceutical composition may be provided in an effective amount to treat the disorder in a subject to whom the composition is administered. As used herein, the phrase "effective to treat the disorder" means effective to ameliorate or minimize the clinical impairment or symptoms resulting from or associated with diabetes and/or obesity.

The amount of pharmaceutical composition that is effective to treat diabetes and/or obesity in a subject may vary, depending on the particular factors of each case, including, for example, the type or stage of the diabetes or obesity, the subject's weight, the severity of the subject's condition, and the method of administration. These amounts can be readily determined by a skilled artisan.

In the method of the present invention, the pharmaceutical composition may be administered to a human or animal subject by known procedures, including, without limitation, oral administration, parenteral administration (e.g., epifascial, intracapsular, intracutaneous, intradermal, intramuscular, intraorbital, intraperitoneal, intraspinal, intrasternal, intravascular, intravenous, parenchymatous, or subcutaneous administration), transdermal administration, and administration by osmotic pump. One preferred method of administration is parenteral administration by intravenous or subcutaneous injection.

For oral administration, the formulation of the pharmaceutical composition may be presented as capsules, tablets, powders, granules, or as a suspension. The formulation may have conventional additives, such as lactose, mannitol, corn starch, or potato starch. The formulation also may be presented with binders, such as crystalline cellulose, cellulose derivatives, acacia, corn starch, or gelatins. Additionally, the formulation may be presented with disintegrators, such as corn starch, potato starch, or sodium carboxymethylcellulose. The formulation also may be presented with dibasic calcium phosphate anhydrous or sodium starch glycolate. Furthermore, the formulation may be presented with lubricants, such as talc or magnesium stearate.

For parenteral administration, the pharmaceutical composition may be combined with a sterile aqueous solution, which is preferably isotonic with the blood of the subject. Such a formulation may be prepared by dissolving a solid active ingredient in water containing physiologically-compatible substances, such as sodium chloride, glycine, and the like, and having a buffered pH compatible with physiological conditions, so as to produce an aqueous solution, then rendering said solution sterile. The formulation may be presented in unit or multi-dose containers, such as sealed ampules or vials. The formulation also may be delivered by any mode of injection, including any of those described above.

For transdermal administration, the pharmaceutical composition may be combined with skin-penetration enhancers, such as propylene glycol, polyethylene glycol, isopropanol, ethanol, oleic acid, N-methylpyrrolidone, and the like, which increase the permeability of the skin to the therapeutic composition, and permit the pharmaceutical composition to penetrate through the skin and into the bloodstream. The pharmaceutical composition also may be further combined with a polymeric substance, such as ethylcellulose, hydroxypropyl cellulose, ethylene/vinylacetate, polyvinyl pyrrolidone, and the like, to provide the composition in gel form, which may be dissolved in solvent, such as methylene chloride, evaporated to the desired viscosity, and then applied to backing material to provide a patch. The pharmaceutical composition may be administered transdermally, at or near the site on the subject where the neoplasm is localized. Alternatively, the pharmaceutical composition may be administered transdermally at a site other than the affected area, in order to achieve systemic administration.

The pharmaceutical composition of the present invention also may be released or delivered from an osmotic mini-pump or other time-release means. The release rate from an elementary osmotic mini-pump may be modulated with a microporous, fast-response gel disposed in the release orifice. An osmotic mini-pump would be useful for controlling release, or targeting delivery, of the pharmaceutical composition.

As used herein and in the appended claims, the singular forms: "a", "an", and "the" include plural references, unless the content clearly dictates otherwise. Thus, for example, reference to "a cell" includes a plurality of such cells and equivalents thereof known to those skilled in the art, and reference to "the compound" is a reference to one or more such compounds and equivalents thereof known to those skilled in the art, and so forth. All publications, patent applications, patents, and other references mentioned herein are incorporated by reference in their entirety.

The present invention is further illustrated by way of the examples contained herein, which are set forth to aid in the understanding of the invention. The exemplary embodiments should not to be construed in any way as imposing limitations upon the scope thereof.

EXAMPLES

Example 1

Materials and Methods

Cell Culture. 3T3-L1 mouse fibroblast were obtained from American Type Culture Collection (Manassas, Va.) and were cultured in Dulbecco's modified Eagle's medium (DMEM) (GIBCO, Grand Island, N.Y.) containing 10% bovine calf serum (BCS) until confluent. Two days after confluency, the cells were stimulated to differentiate with an induction medium (hereinafter "MDI"), which comprises DMEM containing 10% FBS, 167 nM insulin (Sigma), 0.5 µg of isobutylmethylxanthine (IBMX) (Sigma), and 1 µm of dexamethasone (Sigma) for two (2) days. Cells were then maintained on 10% FBS/DMEM with 167 nM insulin for another 2 days, followed by culturing with FBS/DMEM for an additional four days, at which time more than 90% of cells were mature adipocytes with accumulated fat droplets. All media contained 100 U/ml of penicillin, 100 µg/ml of streptomycin, and 292 µg/ml of glutamine. Cells were maintained at 37° C. in a 5% $CO_2$ humidified environment.

Reagents. Phosphate-buffered saline (PBS) and DMEM medium were purchased from GIBCO (BRL Life Technologies, Grand Island, N.Y.). XN, HK, G, and GS ($\geq$98%) were purchased from Sigma (St. Louis, Mo.). ApoStrand ELISA Apoptosis Detection Kit was purchased from BIOMOL (Plymouth Meeting, Pa.). The viability assay kit (CellTiter 96 Aqueous One Solution Cell Proliferation Assay; containing 3-(4,5-dimethythizol-2-yl)-5-(3-carboxymethoxyphenyl)-2-(4-sulfophenyl)-2H-tetrazolium assay reagent (MTS) and Caspase-Glo™ 3/7 assay kit were purchased from Promega (Madison, Wis.). Antibodies specific for polyclonal poly (ADP-ribose) polymerase (PARP), Bcl-2, β-actin, and cytochrome c were from Santa Cruz Biotechnology (Santa Cruz, Calif.).

Cell viability assay. Adipocytes were incubated with dimethyl sulfoxide (DMSO) (0.02%) or test compounds. Prior to measuring viability, treatment media were removed and replaced with 100 µl fresh 10% FBS/DMEM medium and 20 µl MTS solution (Promega, Madison, Wis.). Cells were then returned to the incubator for an additional 2 h before 25 µl of 10% sodium dodecyl sulfate (SDS) was added to stop the reaction. The absorbance was measured at 490 nm in a plate reader (µQuant Bio-Tek Instruments, Inc. Winooski, Vt.) to determine the formazan concentration, which is proportional to the number of live cells.

Apoptosis assays. For the assessment of apoptosis, the ApoStrand ELISA Apoptosis Detection Kit (Biomol, Plymouth Meeting, Pa.) was used. This kit detects single stranded DNA, which occurs in apoptotic cells but not in necrotic cells or in cells with DNA breaks in the absence of apoptosis. Adipocytes were incubated with DMSO or the test compounds for the indicated times and at the indicated concentrations. Thereafter, treatment media was removed and the cells were fixed for 30 min and assayed according to the manufacturer's instructions.

Caspase-3 and 7 activity assay. Adipocytes were incubated with DMSO or the test compounds and the indicated times and concentrations. Thereafter, 100 µl of caspase-Glo 3/7 reagent (Promega, Madison, Wis.) was added to each sample and the cells were incubated for 1 h and assayed according to the manufacturer's instructions.

Western blot analysis. Following the indicated treatment, whole cell extracts were prepared by washing the cells with phosphate buffered saline (PBS) and suspending the cells in a lysis buffer (20 mM Tris, pH 7.5, 150 mM sodium chloride, 1 mM EDTA, 1 mM EGTA, 1% Triton X-100, 2.5 mM sodium pyrophosphate, 1 mM β-glycerophosphate, 1 mM sodium vanadate ($Na_3VO_4$), 1 µg/ml aprotinin, 1 µg/ml leupeptin, and 100 µg/ml phenylmethylsulfonyl fluoride). After 30 min of rocking at 4° C., the mixtures were centrifuged (10,000×g) for 10 min, and the supernatants were collected as whole-cell extracts. To isolate the cytosolic fraction, cells were washed with ice-cold PBS and resuspended in isotonic homogenizing buffer (250 mM sucrose, 10 mM potassium chloride, 1.5 mM magnesium chloride, 1 mM EGTA, 1 mM EDTA, 1 mM dithiothreitol, 0.1 mM phenylmethylsulfonylfluoride, 1 µg/ml aprotinin, 1 µg/ml leupeptin, 10 mM HEPES-KOH, pH 7.4). After 30 min incubation on ice, cells were homogenized with a glass Dounce homogenizer (30 strokes) and centrifuged at 700×g for 10 min. The supernatant was collected as the cytosolic fraction, and the resulting mitochondrial pellets were dissolved in lysis buffer. The protein concentration was determined by the method of Bradford with bovine serum albumin as the standard. Western blot analysis was performed using the commercial NUPAGE system (Novex/Invitrogen, Carlsbad, Calif.). Samples were heated to 70° C. for 10 min, separated by 12% acrylamide gels, and analyzed by immunoblotting. Immunoblots were developed using ECL kit (Piscataway, N.J., USA).

Quantitative analysis of Western blot data. Measurement of signal intensity on PVDF membranes after Western blotting with various antibodies was performed using a FluorChem densitomer with AlphaEaseFC image processing and analysis software (Alpha Innotech Corporation, San Leandro, Calif.). For statistical analysis, all data were expressed as integrated density values (IDV). For PARP, Bcl-2, and cytochrome c, IDVs were calculated as the density values of the specific protein bands/β-actin density values and expressed as percentage of the control.

Statistical analysis. One- or two-way analysis of variance (GLM procedure, Statistica, version 6.1; StatSoft, Inc.) was used to determine significance of treatment effects and interactions. Fisher's post-hoc least significant difference test was used to determine significance of differences among means. Statistically significant differences are defined at the 95% confidence interval. Data shown are means±SEM.

Quantification of lipid content and oil red O staining. Lipid content was measured using a commercially available kit (AdipoRed Assay Reagent; Cambrex Bio Science, Walkersville, Inc.). Briefly, test compositions and a 0.01% DMSO control were added with the induction medium for days 0-6 of adipogenesis. Medium was changed every 2 days. On day 6, intracellular lipid content was measured by AdipoRed Assay. Cells were washed with PBS (pH 7.4) and 200 µl of PBS was added to the wells. About 5 µl of AdipoRed reagent was added to each well. After 10 min, the plates were placed in the fluorometer and fluorescence was measured with excitation wavelength of 485 nm and emission wavelength of 572 nm. To visualize lipid content, treated cells were stained with oil red O and hematoxylin as described by Suryawan and Hu. After mounting with glycerol gelatin, three images for each dish were captured using ImagePro software (MediaCybernetics, Silver Spring, Md.).

Example 2

Effects of Xanthohumol and Honokiol

Effects of XN and HK on cell viability and apoptosis. Adipocytes were treated with XN (25, 50 µM) and HK (25, 50, 75 µM) as individual compounds or in combination for 12, 24, and 48 h. After treatment, cell viability was determined by the MTS assay, as described in Example 1. FIG. 1 is a graph that shows the effects of XN and HK on the viability of mature adipocytes after 48 h. As shown in FIG. 1, while HK (75 µM) alone may decrease mature adipocytes viability, the combinations of XN and HK caused synergistic decreases in mature adipocytes viability. XN and HK alone at 25 and 50 µM had no effect whereas HK at 75 µM decreased cell viability by 9.1±2.5% (P<0.005). Combinations of XN and HK significantly decreased viability in a dose-dependent manner (FIG. 1), and many of those combinations decreased viability more than the additive responses to XN and HK alone (Table 1).

TABLE 1

| Treatment | % Decrease in viability mean ± s.e.m. | % Increase in apoptosis mean ± s.e.m. |
|---|---|---|
| Control | 0.0 ± 1.0 | 0.0 ± 2.4 |
| XN50 | −2.8 ± 1.5 | 51.0 ± 16.5 |
| HK50 | −1.8 ± 1.5 | 10.8 ± 5.9 |
| HK75 | 9.1 ± 2.5 | 70.4 ± 15.9 |
| XN50HK50 (calculated) | −4.6 ± 1.5 | 29.6 ± 13.1 |
| XN50HK75 (calculated) | 6.3 ± 2.5 | 121.4 ± 30.9 |
| XN50 + HK50 (combined) | 63.7 ± 1.5 | 203.8 ± 37.1 |
| XN50 + HK75 (combined) | 78.3 ± 1.3 | 384.4 ± 50.5 |

Figure 2:
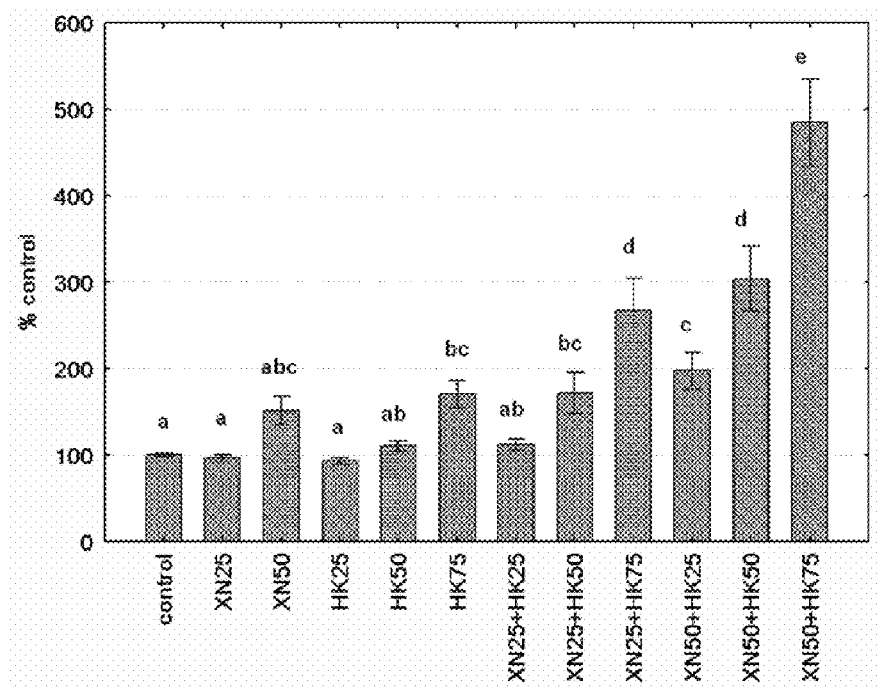
FIG. 2 is a graph that shows the effects of xanthohumol and honokiol on mature adipocyte apoptosis.

Table 1 provides the percent decrease in viability and increase in apoptosis of mature adipocytes treated with XN, HK, and combinations of XN and HK The enhanced reduction in cell viability by XN plus HK was evaluated to determine if the reduction in cell viability was attributable to apoptosis. Twenty-four-hour treatment with either XN or HK alone at 25 and 50 μM had no effect, while HK at 75 μM increased apoptosis by 70.4±15.9% (P<0.05) (Table 1). Combinations of XN and HK significantly increased apoptosis in a dose-dependent manner (FIG. 2), and many of those combinations increased apoptosis more than the additive responses to XN and HK alone. FIG. 2 is a graph that shows the effects of XN and HK on mature adipocyte apoptosis in accordance with one embodiment of the present invention. Means that are not labeled by a common letter are significantly different (i.e., P<0.05). As shown in FIG. 2, while HK (75 μM) alone may increase mature adipocytes apoptosis, the combinations of XN and HK (except for XN (25 μM)/HK (25 μM)) caused synergistic increases in mature adipocytes apoptosis.

Figure 3:
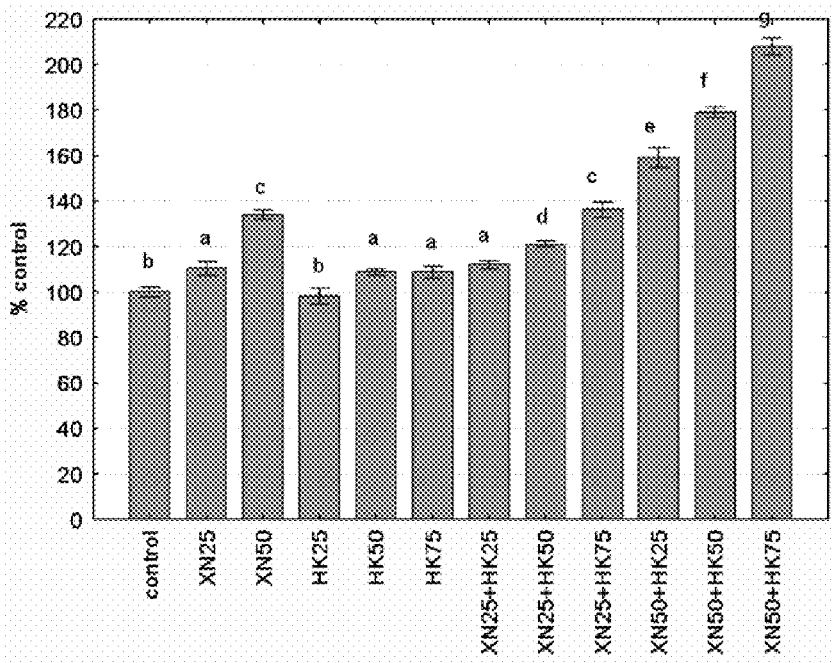
FIG. 3 is a graph that shows the effects of xanthohumol and honokiol on caspase 3/7 activity in mature adipocytes.

Effects of XN and HK on caspase-3/−7 activation and PARP cleavage. To confirm apoptosis in response to combined treatment with XN and HK, the activity of caspase-3/7 was evaluated. Adipocytes were treated for 12 h with XN (25, 50 μM) and HK (25, 50, 75 μM) as individual compounds or in combination. Both XN and HK increased caspase-3/7 activity in a dose-dependent manner (FIG. 3). The combination of XN and HK increased caspases 3/7 activity significantly more than the additive responses to XN and HK alone. As shown in FIG. 3, while both compounds caused small dose-related increases in caspase 3 activity, the combinations of these compounds (e.g., 25/75, 50/25, 50/50, or 50/75 μM, respectively) synergistically increased the caspases 3/7 activity levels in mature adipocytes. Means that are not labeled by a common letter are significantly different (i.e., P<0.05).

Effects of XN and HK on adipogenesis of post-confluent pre-adipocytes during maturation. Post-confluent pre-adipocytes were induced to differentiate for 0-6 days in differentiation medium with or without XN or HK for indicated times. AdipoRed dye was used to determine the effects of both XN and HK on adipogenesis during the maturation of 3T3-L1 pre-adipocytes into mature adipocytes. Means that are not labeled by a common letter are significantly different (i.e., P<0.05).

Figure 4A:
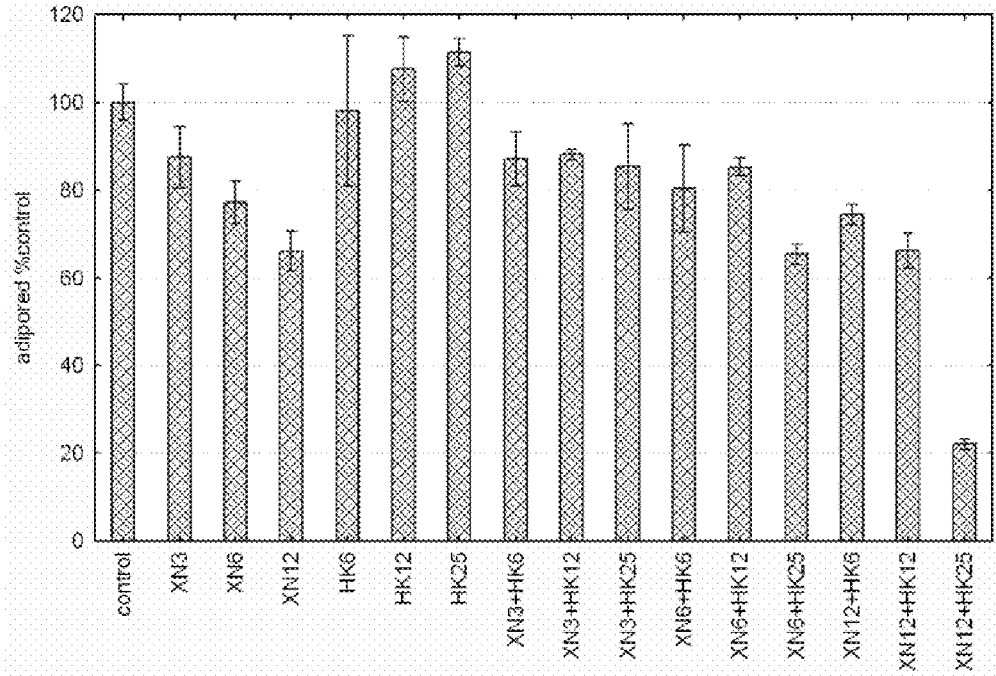
FIG. 4A-B are graphs that show the effects of xanthohumol and honokiol on adipogenesis of post-confluent pre-adipocytes during maturation.
Figure 4B:
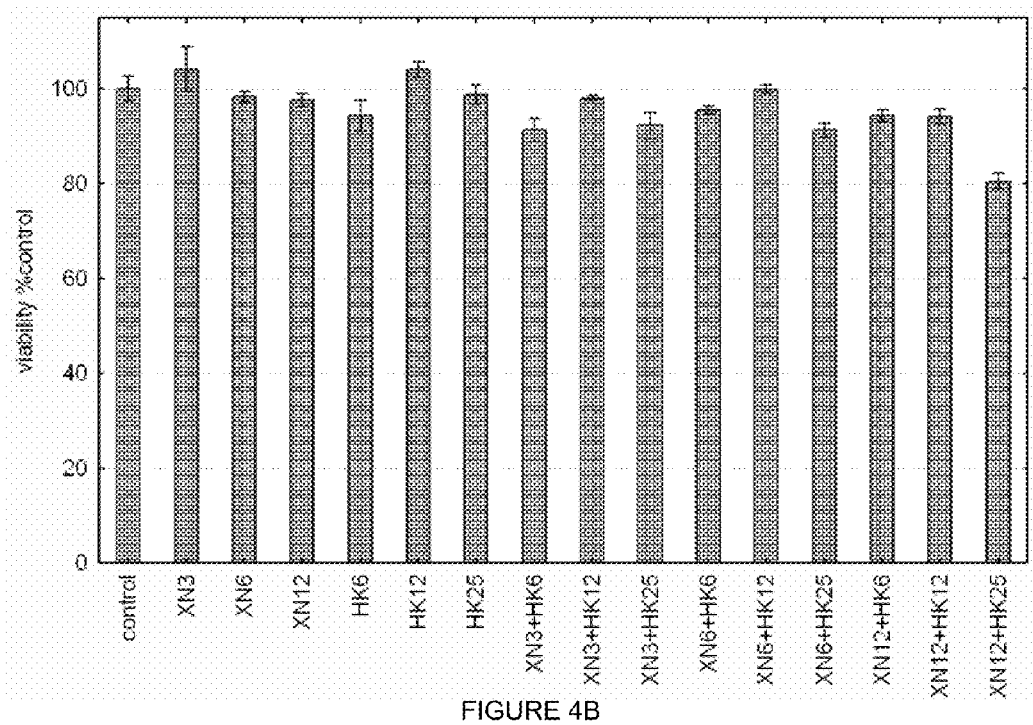

As shown in FIG. 4A, XN alone decreased lipid accumulation; and HK alone increased lipid accumulation during the maturation of 3T3-L1 pre-adipocytes into mature adipocytes. The combination of XN and HK (12 and 25 μM, respectively) synergistically decreased lipid accumulation during the maturation of 3T3-L1 pre-adipocytes into mature adipocytes, which also caused a 20% decrease in cell viability (FIG. 4B). No other treatments significantly affected cell viability.

Figure 5:
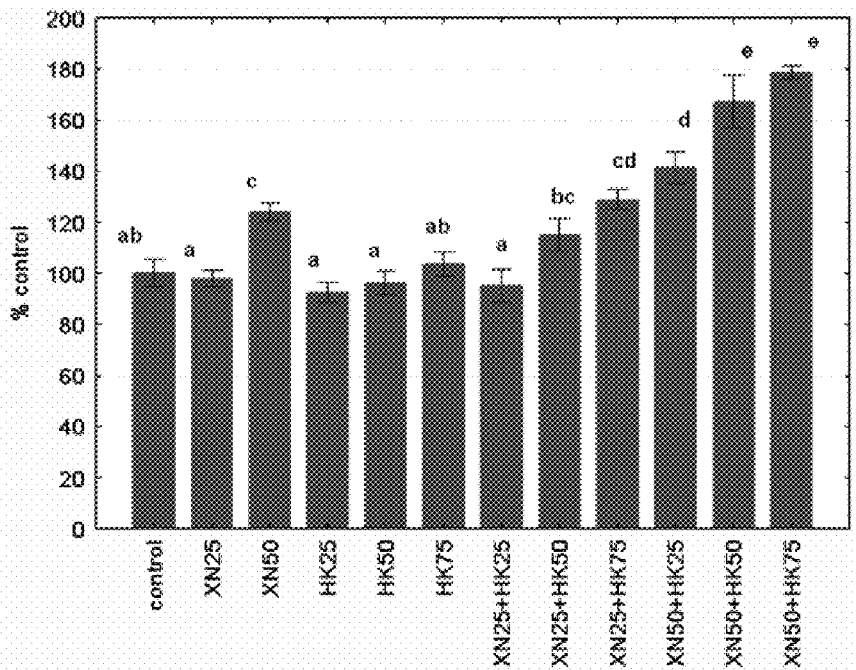
FIG. 5 is a graph that shows the effects of xanthohumol and honokiol on lipolysis of mature adipocytes.

Effects of XN and HK on lipolysis in mature adipocytes. Mature adipocytes were incubated with either control or test compounds for indicated times. FIG. 5 is a graph that shows the effects of XN and HK on lipolysis of mature adipocytes. Means that are not labeled by a common letter are significantly different (i.e., P<0.05). As shown in FIG. 5, while XN (50 μM) alone caused a 20% increase in lipolysis, the combinations of XN and HK synergistically increased lipolysis in mature adipocytes.

Figure 6A:
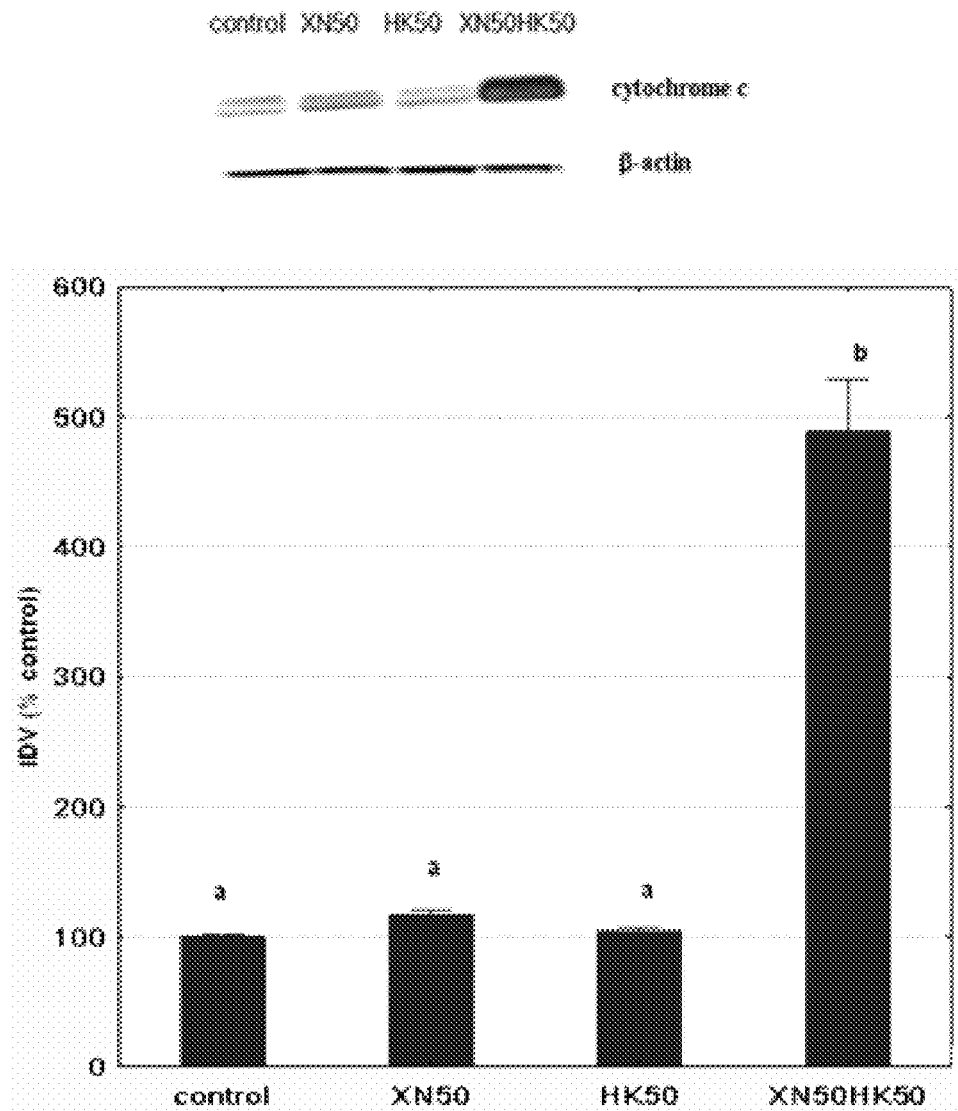
FIG. 6A-B are Western blots and graphs and that show the effects of xanthohumol and honokiol on cytochrome c release from mitochondria and Poly (ADP-ribose) polymerase (hereinafter, "PARP") cleavage in mature adipocytes.
Figure 6B:
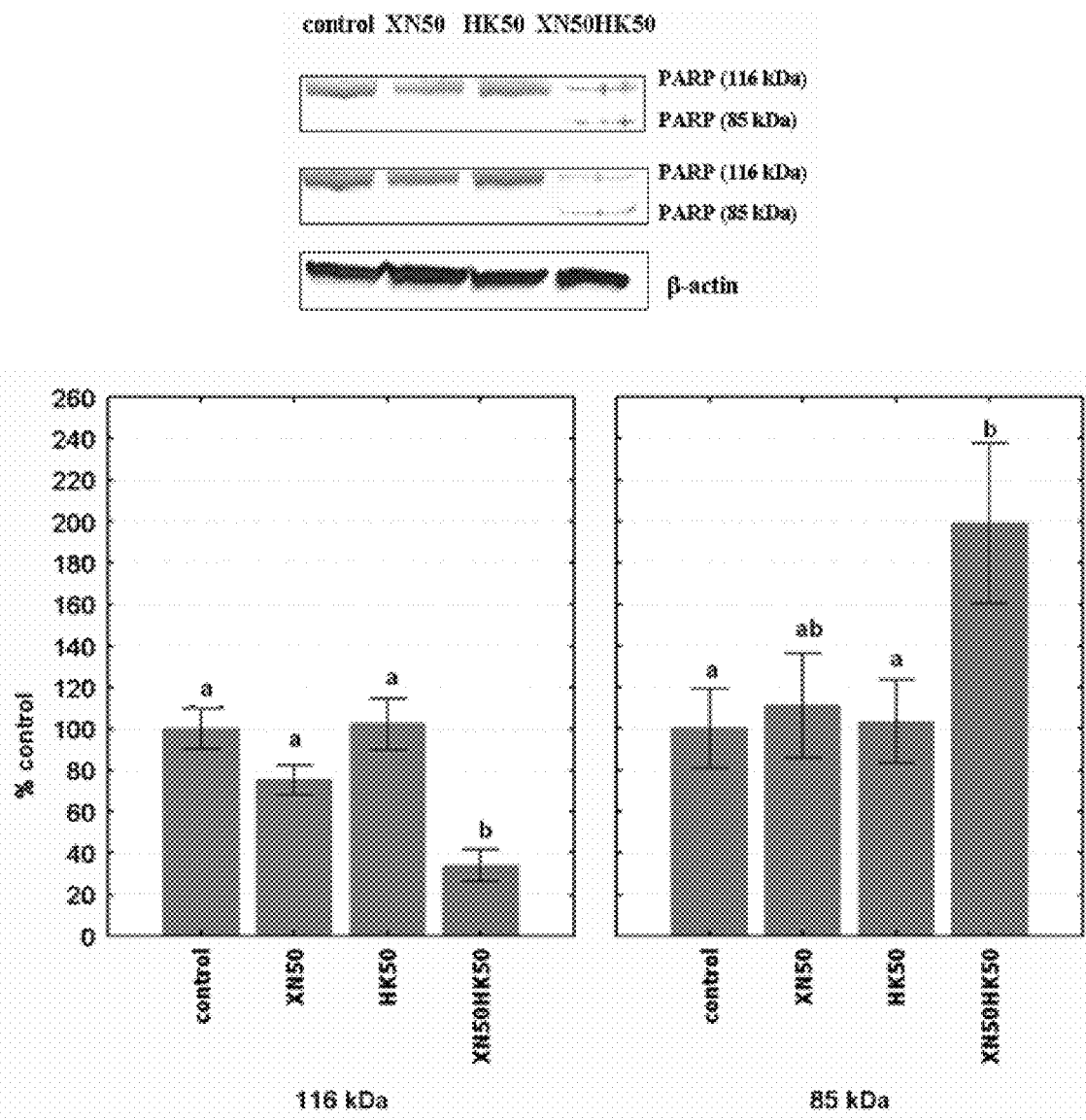

Effects of XN and HK cytochrome c release from mitochondria and PARP cleavage in mature adipocytes. To further investigate whether XN and HK affects the intrinsic apoptosis induction pathway, the induction of cytochrome c release was evaluated by Western blotting. As shown in FIG. 4A, neither 50 μM of XN nor 50 μM of HK had an effect on cytochrome c, but the combination of XN and HK significantly increased its release by 388.7±39.4% (P<0.001). FIG. 6B depicts that, although neither compound alone may affect Poly (ADP-ribose) polymerase (hereinafter, "PARP") cleavage in mature adipocytes, the combination of XN and HK caused a 65% decrease in the original form (116 kDa PARP) and a concomitant 100% increase in the cleaved form (85 kDa PARP). In both FIG. 6A-B, means that are not labeled by a common letter are significantly different (i.e., P<0.05).

Example 3

Effects of Xanthohumol and Genistein

Figure 7:
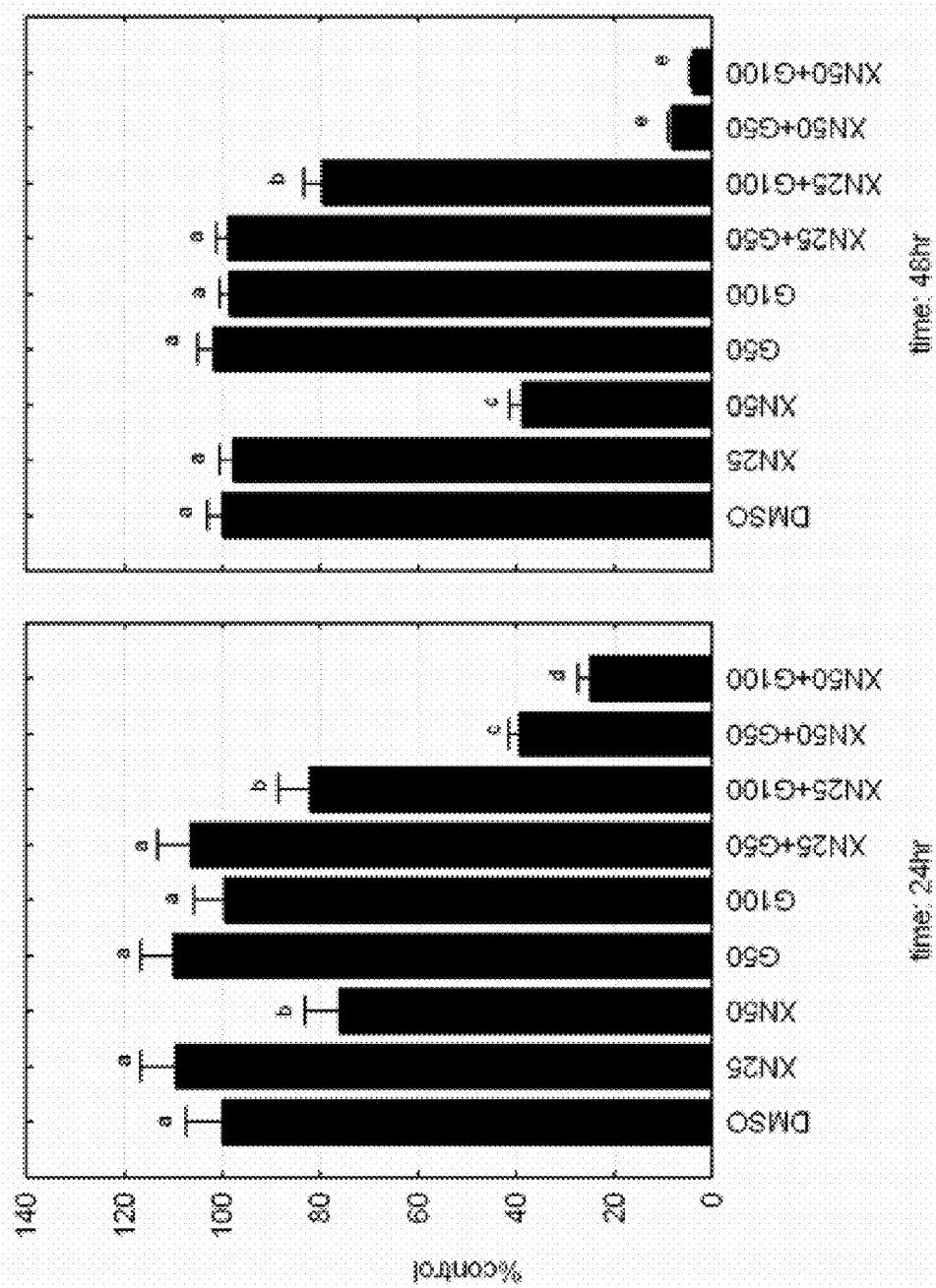
FIG. 7 is a graph that shows the effects of xanthohumol and genistein on mature adipocytes viability.

Effects of XN and G on cell viability and apoptosis. Adipocytes were treated with XN (25, 50 μM) and G (50, 100 μM) as individual compounds or in combination for 24 and 48 h. After treatment, cell viability was determined by the MTS assay, as described in Example 1. FIG. 7 is a graph that shows the effects of XN and G on mature adipocytes viability after 24 h and 48 h. Means that are not labeled by a common letter are significantly different (i.e., P<0.05). As shown in FIG. 7, XN decreased the viability of mature adipocytes in a dose-dependent and time-dependent manner, while G did not affect the viability of mature adipocytes. All combinations of XN and genistein (except for XN25+G50) caused synergistic decreases of the viability of mature adipocytes.

Figure 8:
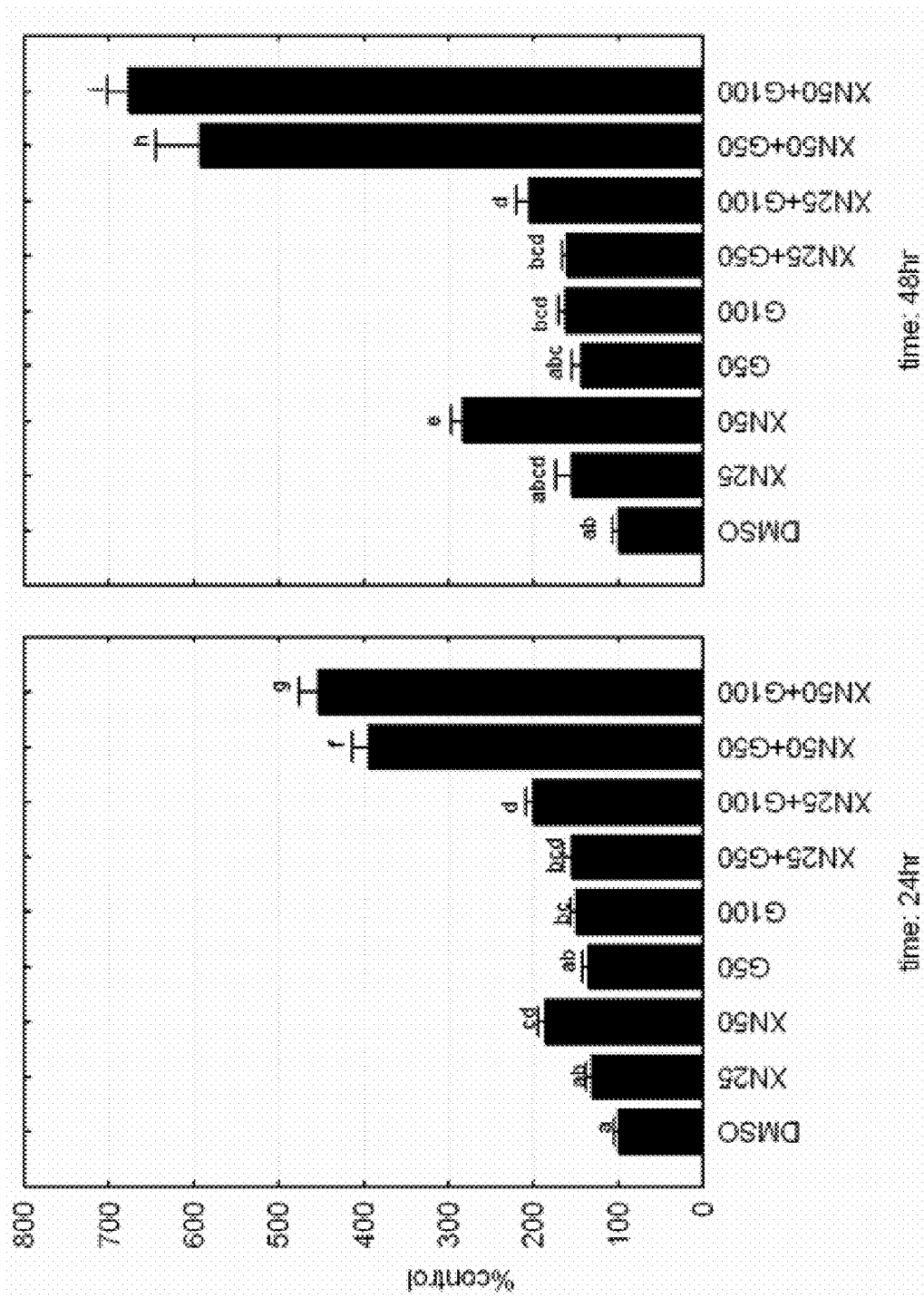
FIG. 8 is a graph that shows the effects of xanthohumol and genistein on mature adipocyte apoptosis.

The effects of XN and G on mature adipocytes apoptosis were investigated by measuring the changes of the levels of single strained DNA (ssDNA) in the cells. FIG. 8 is a graph that shows the effects of XN and G on mature adipocyte apoptosis. As shown in FIG. 8, means that are not labeled by a common letter are significantly different (i.e., P<0.05). XN increased apoptosis of mature adipocytes (see, e.g., XN 50 μM at 48 hrs); however, G alone did not affect apoptosis of mature adipocytes. The combination, however, of XN (50 μM) with G (50 μM and 100 μM) significantly increased the apoptosis of mature adipocytes in a time-dependent manner. See FIG. 8

Example 4

Effects of Xanthohumol and Guggulsterone

Figure 9:
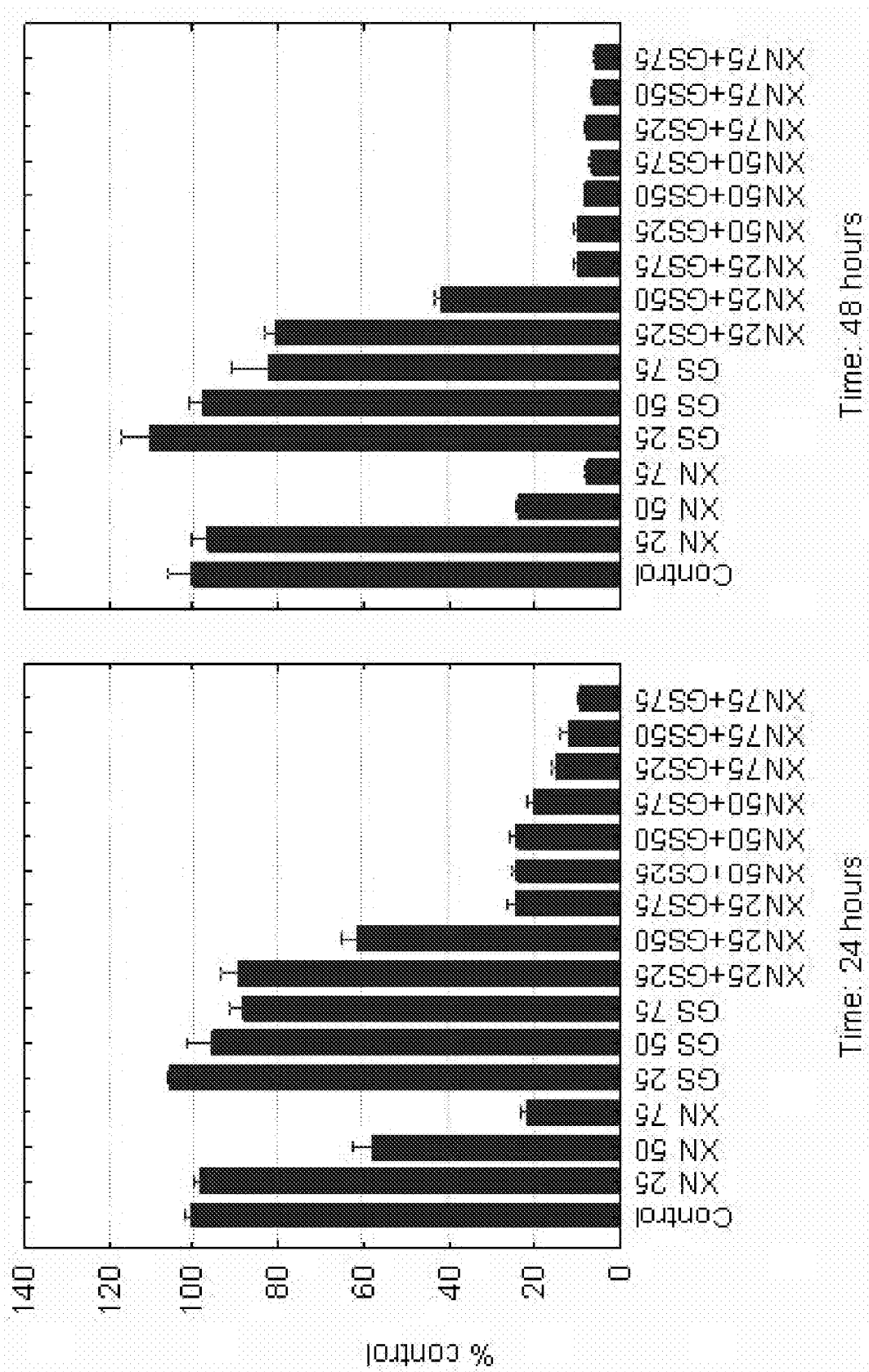
FIG. 9 is a graph that shows the synergistic effect of xanthohumol and guggulsterone on mature adipocyte cell viability.

Effects of XN and GS on cell viability and apoptosis. Adipocytes were treated with XN (25, 50, 75 μM) and GS (25, 50, 75 μM) as individual compounds or in combination for 24 and 48 h. After treatment, cell viability was determined by the MTS assay, as described in Example 1. FIG. 9 is a graph that shows the synergistic effect of XN and GS on mature adipocyte cell viability. Means that are not labeled by a common letter are significantly different (i.e., P<0.05). FIG. 9 shows the effect of XN and GS on mature adipocytes cell viability for the indicated dose after 24 h and 48 h. As shown in FIG. 9, XN and GS decreased the viability of mature adipocytes in a dose-dependent and time-dependent manner. All combinations of XN and GS caused synergistic decreases of the viability of mature adipocytes.

Figure 10:
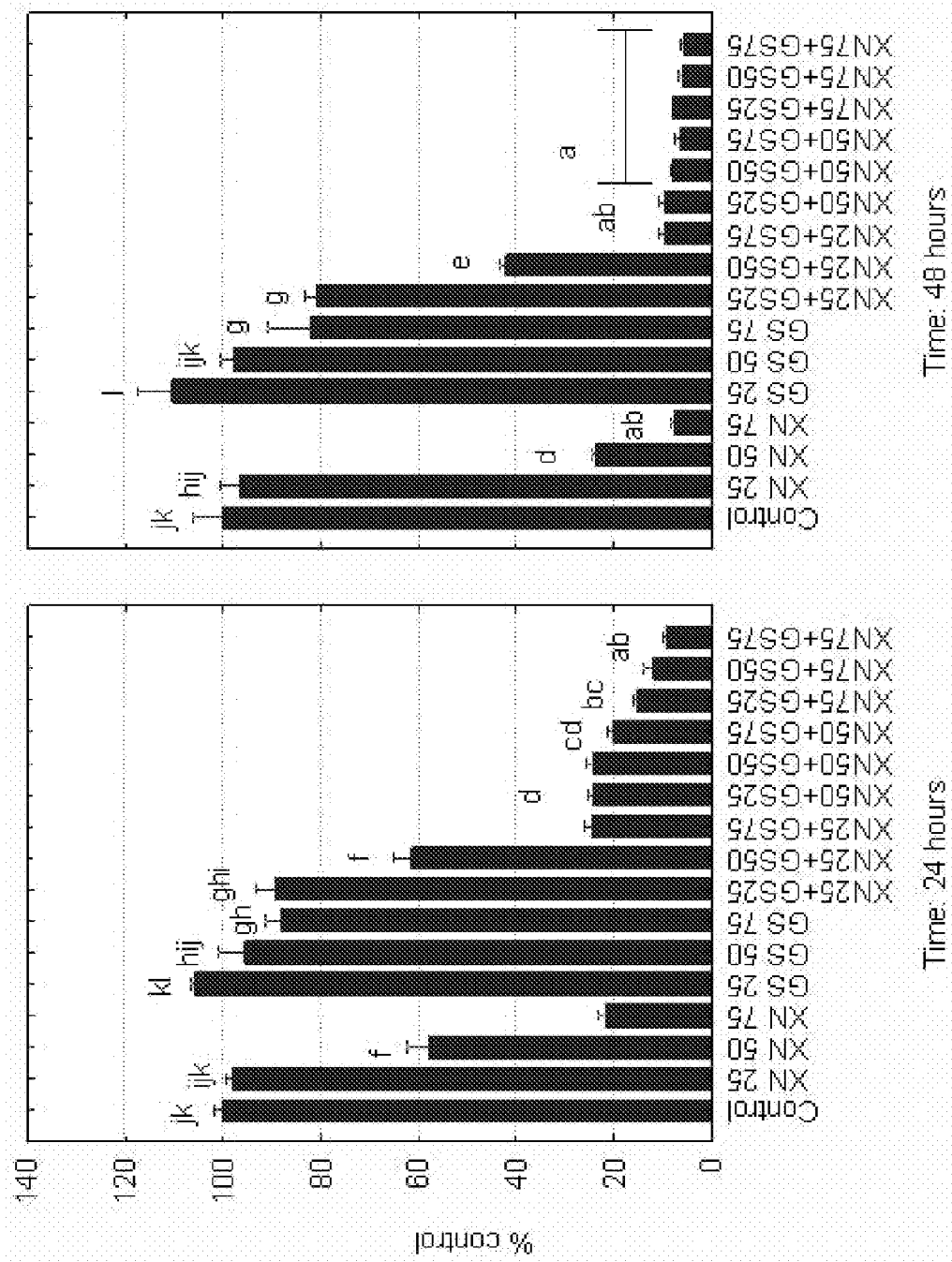
FIG. 10 is a graph that shows the effect of xanthohumol and guggulsterone on pre-adipocyte cell viability.

FIG. 10 shows the data from experiments to determine the effect of XN (25, 50, 75 µM) and GS (25, 50, 75 µM) on pre-adipocyte cell viability after 24 h and 48 h. FIG. 10 is a graph that shows the effect of XN and GS on pre-adipocyte cell viability. Means that are not labeled by a common letter are significantly different (i.e., P<0.05). The pre-adipocytes (FIG. 10) exhibited a similar response to that produced by the mature adipocytes (FIG. 9); however, the pre-adipocytes showed a much greater response to the combination of XN and GS at lower concentrations.

Figure 11:
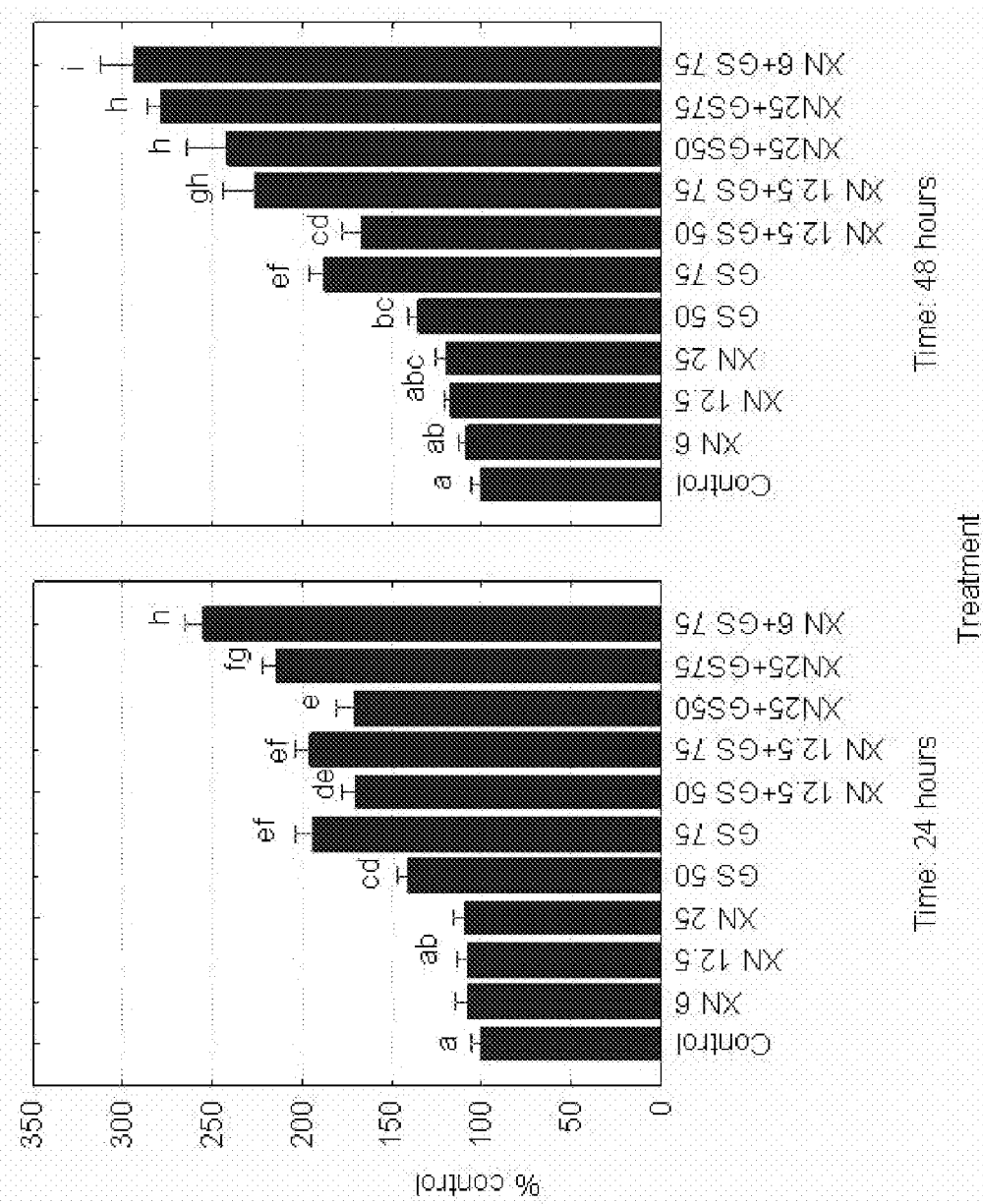
FIG. 11 is a graph that shows the effect of xanthohumol and guggulsterone on mature adipocyte apoptosis.

The enhanced reduction in cell viability by XN plus GS was evaluated to determine if the reduction in cell viability was attributable to apoptosis. FIG. 11 is a graph that shows the effect of XN and GS on mature adipocyte apoptosis. Means that are not labeled by a common letter are significantly different (i.e., P<0.05). As shown in FIG. 11, the combination of XN and GS at 25 and 50 µM concentrations, respectively, increased apoptosis by about 150%, and both XN and GS alone increased apoptosis by about 20%. Cells were also stained with Hoechst stain, and there was a small increase in staining with the individual treatments, but the combination of XN (25 µM)+GS (50 µM) caused a much greater increase in staining.

Figure 12:
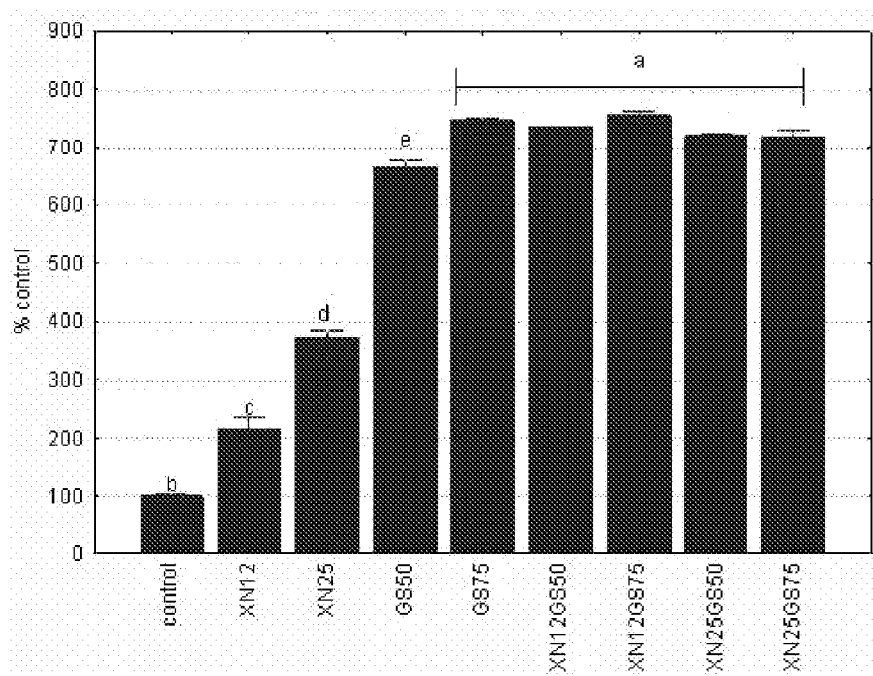
FIG. 12 is a graph that shows the effect of xanthohumol and guggulsterone on LDH release.

FIG. 12 is a graph that depicts the effect of XN and GS and the combination thereof on lactate dehydrogenase (LDH) release. Mature adipocytes were treated with XN 25 and 50 uM and GS 50 and 75 µM 48 hours. LDH levels were measured using commercially available kit (CytoTox-ONEassay, Promega, Madison, Wis.). Means that are not labeled by a common letter are significantly different (i.e., P<0.05). All treatments increased LDH treatment as compared to the control. A synergistic effect may have been masked by achieving a maximum LDH release with these levels of compounds.

Figure 13:
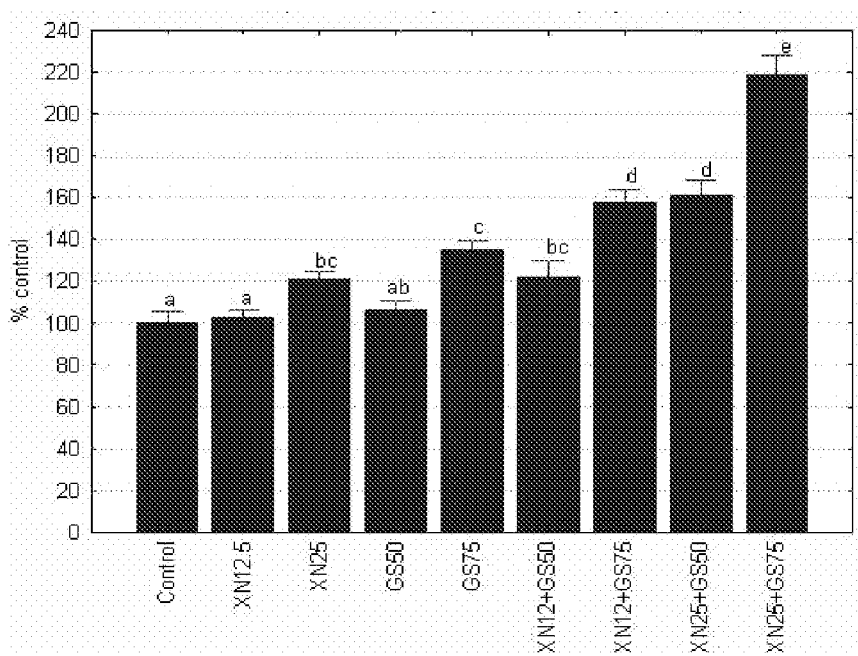
FIG. 13 is a graph that shows the effect of xanthohumol and guggulsterone on caspase 3/7 activity.

FIG. 13 is a graph that shows the effect of XN and GS and combinations thereof on caspase 3/7 activity. Means that are not labeled by a common letter are significantly different (i.e., P<0.05). The caspases 3/7 activity was measured using a commercially available Caspase Glo 3/7 assay kit (Promega, Madison, Wis.), as described in Example 1. GS at 75 µM increased caspase activity, but the other individual treatments were not significantly different from control. All combinations except the lowest concentration combination caused synergistic increases in caspase 3/7 activity.

Figure 14:
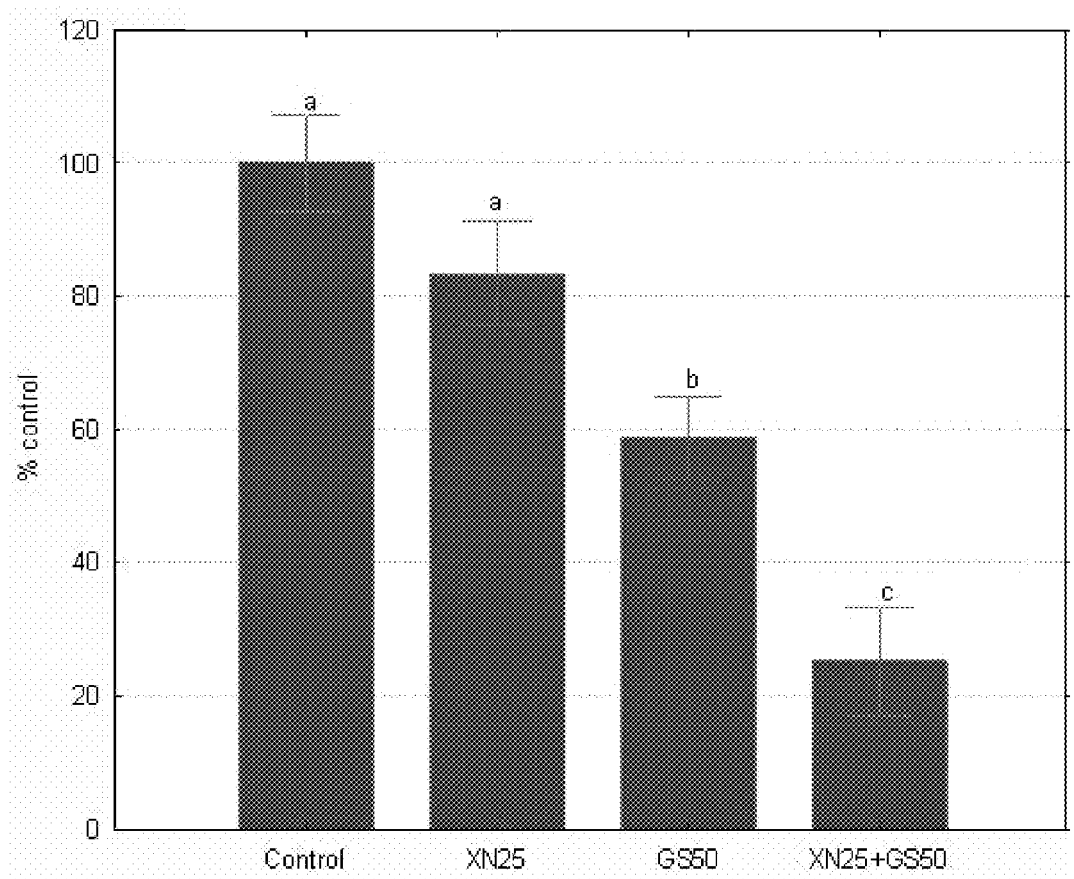
FIG. 14 is a graph that shows the effect of xanthohumol and guggulsterone on Bcl2 protein expression.

To further investigate whether XN and GS affects the intrinsic apoptosis induction pathway, the expression of the anti-apoptotic Bcl-2 protein was evaluated by western blotting. As shown in FIG. 14, both compounds individually decreased Bcl-2, and the combination (XN 25 µM and GS 50 µM) caused at least an additive effect, although the level of Bcl-2 may have been too low to know whether the effect was synergistic.

To determine the synergistic effects of XN and GS on adipogenesis, the effect of XN and GS on inhibiting lipid accumulation in (FIG. 15A) and viability of (FIG. 15B) maturing 3T3-L1 adipocytes was determined. Means that are not labeled by a common letter are significantly different (i.e., P<0.05). XN and GS decreased adipogenesis and lipid accumulation synergistically at very low concentrations in mature adipocytes (FIG. 15A-B). The combination, however, did not show a synergistic effect on decreasing viability in maturing pre-adipocytes (FIG. 16A). FIG. 16A is a graph that shows the effect of XN and GS on viability in maturing pre-adipocytes cell viability. The means denoted by common letters are significantly different (P<0.05). In the oil red O stained cells as shown in FIG. 16B-E, the combination treatment enhanced the decrease in lipid accumulation, and cells had more of a fibroblast appearance.

The effect of XN and GS in inducing lipolysis was shown in FIG. 17A-B. FIG. 17A shows the results of treatment of mature adipocytes with XN 6 µM and 12 µM and GS 12 µM and 25 µM for seven days. Both XN and GS at lower concentrations decreased lipid accumulation in mature adipocytes after 7-days. However, the combinations decreased lipid content in an additive manner. This experiment shows that the lower doses are equally effective in decreasing lipid content in mature adipocytes provided, the incubation period is increased (Compare FIG. 17B (12 h incubation) to 17A (7 day incubation)). Both XN and GS increased lipolysis slightly and the combination caused at least an additive increase in lipolysis as shown in FIG. 17B.

Whereas this invention has been described in detail with particular reference to preferred embodiments, it is understood that variations and modifications can be effected within the spirit and scope of the invention, as described herein before and as defined in the appended claims. The corresponding structures, materials, acts, and equivalents of all means plus function elements, if any, in the claims below are intended to include any structure, material, or acts for performing the functions in combination with other claimed elements as specifically claimed.

What is claimed is:

1. A method of treating obesity in a subject, the method comprising administering to a subject a composition comprising an effective amount of a combination of xanthohumol and at least one of honokiol, guggulsterone or genistein, wherein said combination provides a synergistic effect on one or more of decreasing the viability of adipocytes in the subject, increasing adipocyte apoptosis in the subject, increasing lipolysis in adipocytes of the subject, or decreasing adipogenesis in pre-adipocytes of the subject.

2. The method of claim 1, wherein said synergistic effect is of decreasing the viability of adipocytes in the subject.

3. The method of claim 1, wherein said synergistic effect is of increasing adipocyte apoptosis in the subject.

4. The method of claim 1, wherein said synergistic effect is of increasing lipolysis in adipocytes of the subject.

5. The method of claim 1, wherein said synergistic effect is of decreasing adipogenesis in pre-adipocytes of the subject.

* * * * *